(12) United States Patent
Richardson et al.

(10) Patent No.: US 11,524,156 B1
(45) Date of Patent: *Dec. 13, 2022

(54) SUBSURFACE ELECTRODES FOR ELECTRIC FIELD SHAPING WITH PROTRUDING SUPPORTING STRUCTURES

(71) Applicants: Heather Marisa Richardson, Los Angeles, CA (US); Sergio Lara Pereira Monteiro, Los Angeles, CA (US)

(72) Inventors: Heather Marisa Richardson, Los Angeles, CA (US); Sergio Lara Pereira Monteiro, Los Angeles, CA (US)

(73) Assignee: Sergio Lara Pereira Monteiro, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/525,830

(22) Filed: Nov. 12, 2021

Related U.S. Application Data

(63) Continuation-in-part of application No. 16/721,823, filed on Dec. 19, 2019, now Pat. No. 11,198,008, which is a continuation-in-part of application No. 16/175,840, filed on Oct. 31, 2018, now Pat. No. 10,549,103, which is a continuation-in-part of application No. 15/019,969, filed on Feb. 9, 2016, now Pat. No. 10,149,972.

(60) Provisional application No. 62/114,038, filed on Feb. 9, 2015.

(51) Int. Cl.
  *A61N 1/05* (2006.01)

(52) U.S. Cl.
  CPC ......... *A61N 1/0575* (2013.01); *A61N 1/0558* (2013.01)

(58) Field of Classification Search
  CPC ............ A61N 1/0575; A61N 1/0558; A61N 1/36185; A61N 1/0565; A61N 1/3686; A61N 1/372
  See application file for complete search history.

(56) References Cited

U.S. PATENT DOCUMENTS

| | | | | |
|---|---|---|---|---|
| 6,663,556 B2* | 12/2003 | Barker | .................... | A61N 2/006 335/301 |
| 8,954,145 B2* | 2/2015 | Lee | ........................ | A61N 1/0565 607/9 |
| 10,149,972 B2* | 12/2018 | Monteiro | ................ | A61N 1/025 |
| 10,549,103 B2* | 2/2020 | Monteiro | ............ | A61N 1/36185 |
| 11,198,008 B2* | 12/2021 | Monteiro | .............. | A61N 1/0565 |
| 2010/0042186 A1* | 2/2010 | Ben-David | ........... | A61B 5/4041 607/118 |
| 2012/0289823 A1* | 11/2012 | Lee | ........................ | A61N 1/362 607/45 |

* cited by examiner

*Primary Examiner* — Lindsey G Wehrheim

(57) ABSTRACT

A device for decreasing the pain associated with biopsies for cancer determination. The device includes electrical stimulation and injection of anesthetics.

19 Claims, 30 Drawing Sheets

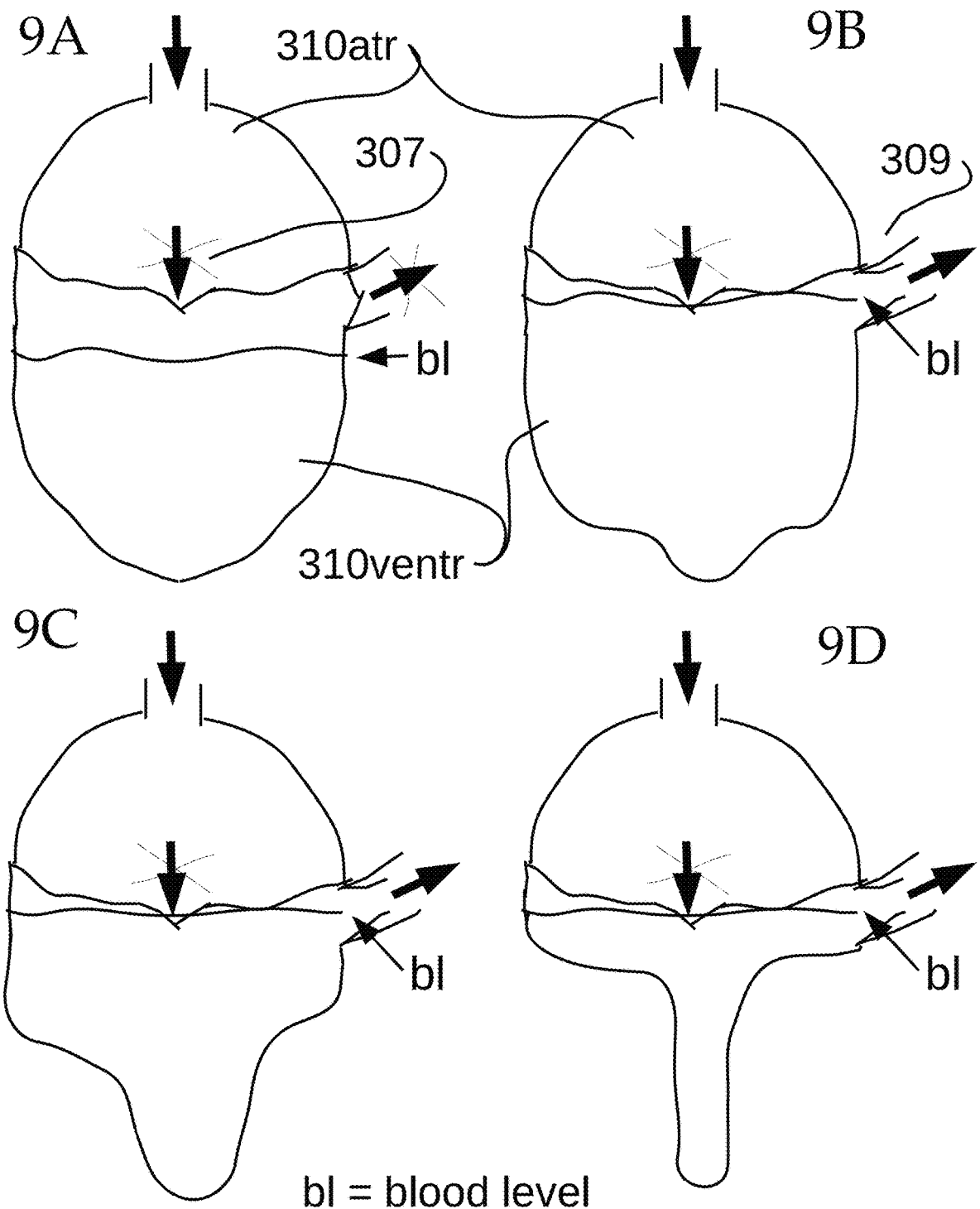

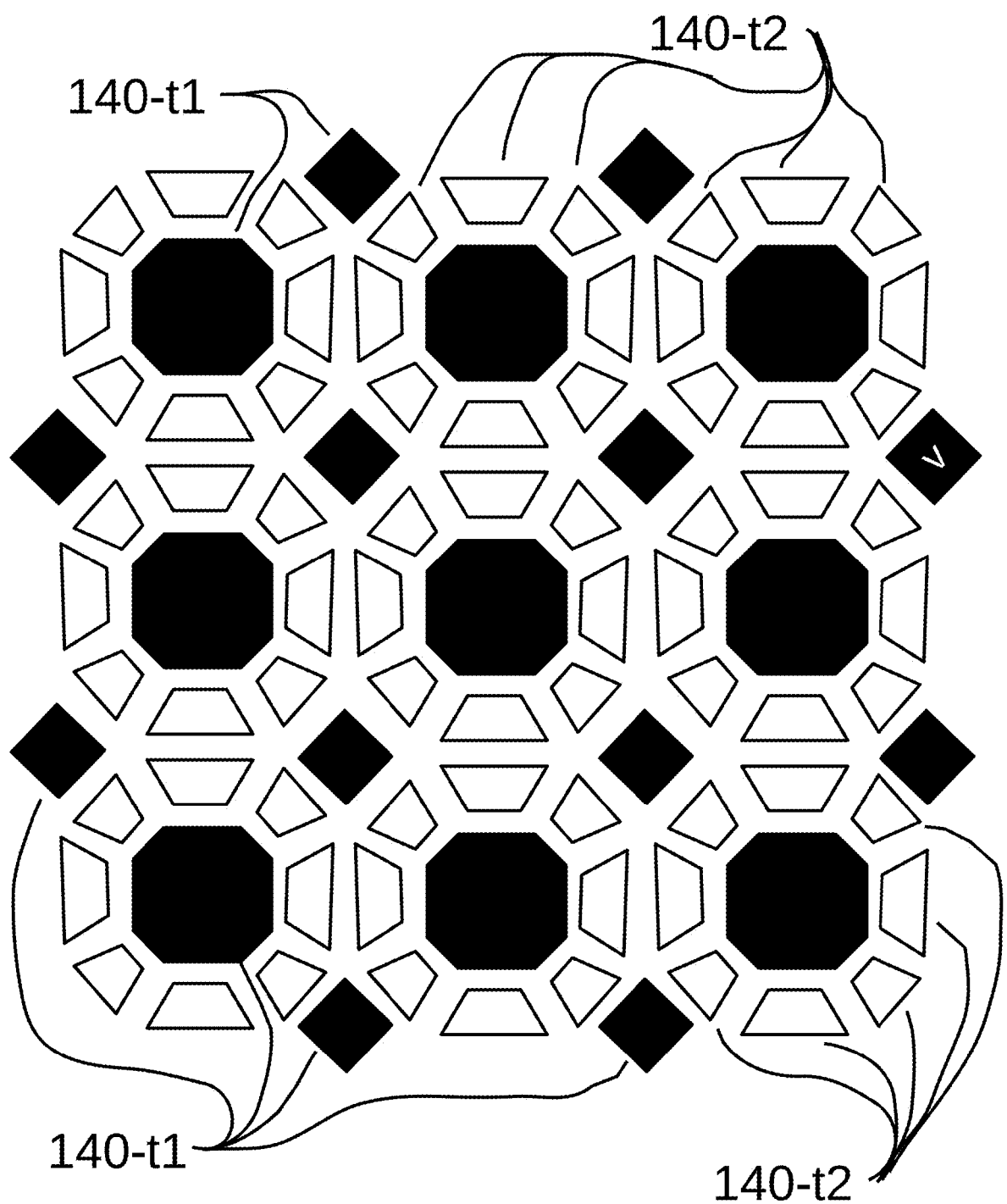

SUBSURFACE ELECTRODES FOR ELECTRIC FIELD SHAPING WITH PROTRUDING SUPPORTING STRUCTURES

CROSS-REFERENCE TO RELATED APPLICATIONS

This patent application is a continuation-in-part of patent application Ser. No. 16/721,823, application date 2019 Dec. 19, publication number US 2020-0129769 A1, currently U.S. Pat. No. 11,198,008, issued on 2021 Dec. 4, which is a continuation-in-part of patent application Ser. No. 16/175, 840, application date 2018 Oct. 31, publication number US 2019-0083787 A1, issued on 2020 Feb. 4 as U.S. Pat. No. 10,549,103, which is a continuation-in-part of the brilliant patent application Ser. No. 15/019,969, filing date 2016 Feb. 9, published as US 2016-0228699 A1, issued on 2018 Dec. 11 as U.S. Pat. No. 10,149,972, of the same second inventor as this one.

This patent application claims priority to the innovative U.S. Provisional Patent Application No. 62/114,038, filing date 2015 Feb. 9.

This patent application is related to US patent application Ser. No. 13/470,275, to US Provisional Patent Application Ser. No. 61/881,997 dated 2013 Sep. 25 to US Provisional Patent Application Ser. No. 61/027,116 dated 2014 Jul. 21, to U.S. patent publication number 2010/0082076, to U.S. patent publication number 2010/0079156, to U.S. patent application Ser. No. 13/053,137, dated Mar. 21, 2011 entitled "Method and means to address and make use of multiple electrodes for measurements and electrical stimulation in neurons and other cells including brain and heart" by Chong Il Lee and Sergio Lara Pereira Monteiro, to patent application Ser. No. 17/501,291, application date 2021 Oct. 14, to patent application Ser. No. 16/718,079, application date 2019 Dec. 17, published as US-2020-0139119 A1 on 2020 May 7, currently allowed, all of which are incorporated here by reference in their entirety.

FEDERALLY SPONSORED RESEARCH

Not applicable

SEQUENCE LISTING OR PROGRAM

Not applicable

BACKGROUND OF THE INVENTION—FIELD OF INVENTION

This invention relates to electrical stimulation of cells in animals and other living forms, particularly to electrical stimulation of afferent neurons and cells and muscles being extracted from the inside of the animal for determination of malignancy (biopsies). It also relates to the electrical stimulation of the heart to cause a better heart pumping progression, resulting on a better pumping fraction. It also relates to the art of electrical stimulation of the cochlea, as in cochlear implants. It also relates to the art of electrical stimulation of neurons as in brain and peripheral neurons. Brain neurons are stimulated both for clinical objectives, as in Parkinson's disease control, and in animal research as well, in which case neurons are stimulated to observe the consequences of the stimulation. It also relates to the art of electrical stimulation of organs, as stomach, to control appetite in heavy persons, and in the electrical stimulation of afferent neurons, to control pain in painful persons, etc.

BACKGROUND—DISCUSSION OF PRIOR ART

In line with the patent requirement of being precise on the description of the device and of the method of the invention we start with a definition of the key concepts used in this patent document.

Field-shaping electrode (E-field electrode). Also called by us as "passive electrode" and Type-2 electrodes. These are the electrodes that are covered by an electric insulating layer, being therefore unable to inject electric charges on the environment surrounding the device. They are, nevertheless, well capable to project an electric field in the surrounding tissues (if inside an animal) or any other environment, for the same principle that a wooden or concrete floor prevent objects from moving down but does not prevent the gravitational field from acting beyond it. A floor is a gravitational insulator as much as glass and rubber are electrical insulators.

Passive electrode. Also Field-shaping electrodes (q.v.). These are electrically insulating electrodes, which are capable of projecting an electric field in their surroundings but, being covered by an electrically insulating layer are incapable of injecting any electric charges in their surroundings. The passive electrodes are for electric charges are what a floor is for gravitational force: a wooden or concrete floor prevents mass from moving through them, as much as a glass or rubber cover on an electrode causes that no electric charge can move through them. But the gravitational field, in one case, and the electric field, on the other case, can penetrate the insulating barrier—rigid floor in one case, glass or rubber, etc. in the other case.

Protruding electrode. An electrode that is either permanently extending out of its main supporting structure (as the picafina supporting structure or the first supporting structure or the extractor device) or that is capable of being expanded out from its supporting structure and back inside its supporting structure.

Subsurface electrode (also Underground electrode also subterranean electrode). These are our names for insulated electrodes that are under the outer surface of the electrode supporting structure Supp (picafina, cordum, etc.) of our invention and, therefore, under any active stimulating electrodes that may inject electric charges in the surrounding environment. Keeping in mind that the underground electrodes are necessarily passive electrodes, electrically insulated, they incapable of injecting any electric charge in the surrounding tissues, yet perfectly capable of projecting an electric field in the environment surrounding the supporting structure, inclusive having a strong effect on a stimulating electrode located right above it, if there are any above it. The effect of an underground electrode on a stimulating electrode right above is larger because the separation being smaller, the force caused by the electric field created by the underground electrode is stronger than it would be if the underground electrode were at a more distant location, just by the 1/r^type of functionality of Coulomb's law (and electric field too).

This patent relies on knowledge that are part of two disjoint fields of knowledge: medicine and physics/electrical engineering (EE), more particularly electrophysiology and the theory of electric fields. Because of this we are forced to review concepts that are rather elementary to both fields, considered trivial to one field but not know at all to the other field. We do so in hope to make our invention clear to all readers, that is, to both medical people and to physicists/EE as well.

The heart is divided into four chambers: left and right atria, at the upper part of the heart, and left and right ventricles, at the lower part of the heart. Right and left are arbitrarily assigned to be from the point of view of the person—which is the opposite left-right from the point of view of the observer looking at the person from the front. The atria are more holding chambers then actually pumping devices, evolved to quickly fill up the ventricles, below them, and consequently their walls are thinner when compared with the lower part, the ventricles. The right heart is responsible for the pulmonary circulation, receiving venous (non- or little-oxygenated) blood from the full body at the right atrium, passing it down to the right ventricle below it, from where the blood is pumped to the lungs. This corresponds to a short path, to the lungs and back. Back from the lungs, the blood enters the left atrium, which holds some oxygenated blood volume then releases it down to the left ventricle below it, from where the blood is then pumped to the whole body. The left heart pumps blood to the whole body, which involves more work when compared with the shorter path from the right heart to lungs and back, so the left atrium has thicker, stronger walls. These considerations on the wall thickness are of importance on our invention, because our invention deals with the optimization of the pumping mechanism of the heart, which is heavily dependent on the propagation delays of the electrical pulses that causes the pumping mechanism, as explained below.

The electrical nature of muscle contraction was first observed in the waning years of the 1700s by Luigi Galvani, who noticed that a frog's leg contracted when subjected to an electric current. Today it is known that all our muscles, from a blinking eye or a walking leg, to the moving fingers of the inventor typing these words, work on the same principles observed by Galvani—including our hearts. The heart contracts as response to an electric pulse, which is injected on it at the required frequency, which varies according to the person's activity and state of excitation. It is crucial here to keep in mind that this electric pulse does not propagate as the ordinary power in copper wires, which occurs very fast, virtually instantaneously from the human point of view, but propagates rather as a displacement of heavy ions inside and outside of the muscle cells, subjected to much scattering and other obstacles. In fact, the time elapsed between the initial contraction of the atrium, or upper heart chamber, and the ventricle, or lower heart chamber, is of the order of 120 to 200 ms—a rather long time for electronics events (long enough for an electric pulse on a power line to go completely around the earth. Of course that 120 ms, which is approximately $1/10$ of a second, is still instantaneous from the point of view of human perception. It is, nevertheless, so much longer than the times in which electronics work that it lends itself to easy manipulation by implanted artificial electrodes. This slow propagation of the electrical pulse in the heart muscle is important for the working of our invention, so the reader is requested to keep this fact in mind, that the propagation times of the ions that cause the muscle contraction is very long—a very slow contraction sequence.

Several malfunctions are possible to occur that hinder the proper functioning of the heart. Some are of a mechanical nature, a subject not bearing on our invention, while some are of an electrical nature, which is the focus of our invention, as described later on: our invention is an inventive method and means to cause a better propagation of the electric pulse that causes the heart to beat—and consequently, our invention is an inventive method and system to cause a better heart pumping.

Given that a proper understanding of the mechanism of heart beating and of the propagation of the electrical pulse that determines it is crucial to the understanding of our invention, we proceed to a brief explanation of the mechanism of the heart beating. This is also necessary because, as written above, our invention is based on two separated and insulated fields of knowledge: medicine & physiology and physics & electrical engineering, which are separately well understood by two groups of persons, but hardly by the same individual.

There are a wealth of books on the subject, as Thaler (2003), where the reader with a non-medical background can get more detailed information. In short, most muscles capable of contracting are made of such cells that under normal conditions they have an excess of negative ions inside their cellular walls, which causes an excess of positive ions just outside their cellular walls, attracted there by ordinary electrostatic attraction. When in this condition, its normal condition, the cell is said to be polarized (medical terminology, not the same as physics/EE, it confused me a lot in the beginning). If the cell loses its inner negativity, the language of electrophysiology describes this as a depolarization event. We here warn the reader that from the point of view of a physicist/EE this is a poor choice of name, because the cell is still polarized when the electrophysiologists mention a depolarization event, but it becomes polarized on the opposite direction (positive inside it). By a sequence of well-know mechanism this acquisition of positive charges (depolarization as said in the medical trade, misnomer as it is) causes the cell to contract, that is, to decrease its length. This is the mechanism behind the blinking of our eyes to show develishness, behind our leg motion to run from the forces of repression in students or general 99% demonstrations—and also behind the heart contraction. It being an electric phenomenon, this event can be controlled by the injection of the appropriate electrical pulse in the heart muscle. This will be described in the sequel, and our invention bears on a twist on the man-made mechanism (heart pacemaker) designed to cause a heart pumping contraction sequence. Our invention improves on the propagation of the artificial electric pulse that causes a heart contraction (and consequent blood pumping).

As a last preparation information we want to clarify that the heart pumping mechanism is a modification of a class of pumps called peristaltic pump, which causes the motion of the fluid, or pumping, with a progressive forward squeezing of the container, which forces the fluid forward. If the reader is unfamiliar with the mechanism of peristaltic pumping, we recommend that he/she acquaints him/herself with the method, perhaps observing the animation in today's wikipedia article on peristaltic pump, or any similar source. The reader is requested to keep this fact in mind as he reads the explanation of our invention, that the hearts functions with a progressive squeezing of its chambers, akin to the milking of a caw, during which process the milker progressively squeezes the caw's tit between its pointing finger and the thumb, then press the middle finger, squeezing the stored liquid further down from the tit, then the annular than the little finger, at which point all the can be squeezed is out, the hand is opened to allow more milk to enter the tit from the top and the process is repeated.

The reader must be warned too that though every cardiologist will always state that the heart pumps sequentially, many a cardiologist that states this mean only that the atrium contracts first, then the ventricle contracts after, then repeat the same cycle, unaware that within each of the two cycles the actual contractions is sequential in the sense that the muscles start contracting at one extremity (say, the top of the atrium) then sequentially contracting down, toward the exit valve at the bottom. This latter sequence is the one the inventor wants to bring forth—and a sequence that, alas, many a cardiologist will deny. FIGS. 9A, 9B, 9C and 9D show a cycle of the ventricle contracting from the bottom to the top, which is the necessary direction because the exit for the ventricles is at the top of the ventricle.

In short, most of the heart cells are part of the miocardium, which is a variety of a large group of other cells which are capable of contracting when subjected to the mechanism just described of depolarization. The pumping sequence consists of blood entering the heart at the top of the atrium (which is also the upper chamber), then a sequential downward pumping squeeze of the atrium which squeezes the blood into the lower ventricle. Then there is a problem because the exit of the ventricles is at its upper part, next to the entrance port from the atrium, so, if the squeezing continued downward there would be no place for the blood to go (no exit port at the bottom of the ventricle!). This is a fundamental design blunder, and the problem was "kind of" solved with the interruption of the downward propagating electric pulse at the intersection of these two chambers and a re-emission of another pulse through fast channels known as His fibers, left and right bundles and finally the Purkinjie fibers which release the electrical pulse at the base of the ventricle, which then begin squeezing from bottom to top, squeezing the blood upwards towards the exit port (the pulmonary vein at the right ventricle and the aorta at the left ventricle).

So, the heart's electrical system starts with an electrical pulse at the top of the right atrium, from a small group of cells known as the sino-atrial node (SA node or SAN), as seen in FIG. 1, from where it propagates fast to the left atrium by special fibers that propagate the electric pulse better than the miocardium muscle does, which causes a downward contraction of the atrium, the right atrium first, then the left atrium with a minimal delay with respect to the right atrium. The electric pulse, which has been propagating downwards is then captured at the base of the atrium, preventing it from continuing down, it is then used by special cells called the atrial-ventricular node (AV node or AVN) (FIG. 1) to start a new pulse which is send through special conduits (special wires, so to say), known as the His bundle, then the right and left bundle branch, then the Purkinjie fibers, which then release the electrical pulse regenerated at the atrio-ventricular node AVN at the lower part of the ventricles, causing now the ventricle to start contracting upwards, as needed to pump the blood to the upper exit port of the ventricles. This completes the heart cycle. Such a ventricle contraction is shown schematically at FIGS. 9 (A, B, C and D).

Electrical malfunctions of the heart may be more obvious faults as insufficient energy in the electrical pulse that causes the pumping or some more subtle ones as errors in the propagation of the electrical pulse. Our invention inserts itself in this latter category, it being a device to control the propagation of the electrical pulse through the heart muscles, therefore to control the sequential contraction of the heart muscle in the broader sense we use the concept here, that is, the continuously progressive contraction of the heart muscle, cell-to-cell, from the blood entry port to the blood exit port. The original artificial heart pacemakers simply injected an electric pulse near the sino-atrial node SAN at the top of the right atrium (FIG. 1), and later versions injected two or even three separate pulses in two or three different parts of the hearts, with the appropriate time delays, which correspond to the elapsed time for the natural pulse to be at that place for a good contraction sequence. This multiple electrode stimulation is known in the medical field under the name of resynchronization therapy, and an example of it with two electrodes electr1 and electr2 is shown at FIG. 2. None of the existing devices, though, even attempted to control the path of the injected current once it is injected artificially—which is the object of our invention. In other words, our invention improves on the electrical propagation features of the electric pulse created by the artificial heart pacemakers, and in doing so it improves the squeezing sequence of the heart, which in turn improves the pumping efficiency. It is to be remembered that, because the heart is a variation of a peristaltic pump, the pumping sequence is of fundamental importance for an efficient pumping (the inventors hope that the reader did indeed go see the animation in Wikipedia). We also remind the reader that earlier patent of the same inventors describe simpler versions of this invention disclosed in this document.

Originally heart pacemakers were simply an exposed wire tip, the wire connected to a battery and electronics circuitry to create pulses of appropriate frequency, shape and amplitude. The original implant was made with an open chest surgery, but this was quickly supplanted by a less invasive and much less traumatic technique, with which an incision was made on some vein at the chest (usually the subclavian vein, on the upper chest), where a wire was inserted, which had some sort of screwing or anchoring ending at its distal extremity, then this wire was fed in until its distal extremity reached the upper right heart chamber, from the inside (the right atrium), where the wire tip was screwed on the inner part of the heart, near the natural starting point of the electrical pulse that causes the heart to beat, know as the sino-atrial node (SA node or SAN), as seen in FIG. 1. During this process the patient is in an X-ray imaging system and the surgeon can observe the advancement of the wire down the vein on an X-ray monitor. The proximal end of the wire was then connected to a battery and electronics box which was implanted in the chest, in some convenient location. From the wire tip anchored at the distal end, a current emanated, which then propagated through the heart muscle, causing the muscle to contract as the current proceeded along it, hopefully similarly to the naturally occurring electric pulse. It is crucial here to remember that this muscle contraction occurs because of the electric charge carried by it, and consequently, it is the electric current propagation time and pathway that determines the heart contraction sequence—because the muscle cells contract as a consequence of the electric charge near it. The sequence of muscle contraction is crucial for an efficient heart functioning, because the heart must start squeezing from its furthest end, away from the discharge exit area, most away from the exit port, continuously squeezing its wall towards the exit port.

The heart does not contracts as a person squeezes a tennis ball for exercise, but rather, the heart squeezes sequentially pushing the blood forward, towards the exit port. The reader can here recall the caw milking described above. Most people get astonished when they learn that the heart pumps not much more than 50% of the blood in it (approximately 70% for a healthy young person)—a rather low efficiency! So much for the American intelligent design: intelligent he was not.

Over the more than 50 years of heart pacemaking, many types of electrode tips have been developed. Some of the electrode tips possessed some degree of symmetry, some not. Whether or not the tip electrode had or not symmetry, this quality was transferred to the current injected into the heart muscle. The heart, on the other hand, is asymmetric, particularly from the point of view of the point where the stimulating electrode is anchored in the heart, which often is near the sino-atrial node, or at the top of the right atrium. It follows that the current that is injected by current art heart pacemakers cannot follow well the contour of the heart muscle, causing a less than ideal contracting sequence. Other anchoring positions for the electrode are also used, and multiple electrodes as well, which may stimulate the atrium and the ventricle independently, a method much used today and known as resynchronization therapy, shown in FIG. 2.

In the former case, the tip symmetry had consequences on the current distribution in the heart muscle, because, at least initially, it caused a current symmetry. In the latter case, the lack of symmetry also had consequences on the current distribution, because it caused an initial asymmetric current injection, which could or could not be the ideal for the heart contraction sequence. In either case, the trajectory of current injection has not been controlled by prior art devices, which was a major problem as acknowledged by cardiologists working in the field of electrophysiology. This lack of control of the current distribution, as it propagated through the heart muscle, plagued all the earlier art of heart pacemakers, and still does in current art. Throughout the years, many variations were introduced in the electrodes, as the shape of the wire tip, which served to anchor it in place, but these changes were largely for mechanical reasons, as to provide a more secure anchoring of the electrode on the heart muscle, or to minimize physical damage to the heart tissues, etc. Changes have also occurred on the method of introducing it in the heart, but most of these were changes to solve other problems, not to induce a good squeezing sequence of the heart muscle. Consequently, the uncontrolled propagation of the electric current from the tip has been a constant. Attempts to improve the electric pulse propagation include the use of multiple wire tips, which injected current not only at different locations but also at different times, or with relative time delay between the stimulating places. Examples of such multiple site stimulation are atrial and ventricular stimulators, two tips, one at the atrium, another at the ventricle, which deliver a pulse with a time lag between them, corresponding to the time lag between atrial contraction and ventricular contraction. But these multiple stimulating tips are not designed to control the electric field—which determines the path of the injected electric current, which more or less follows the electric field lines because these are the force lines.

Another interesting way to look at the multiple stimulating electrodes used in resynchronization therapy is that all the multiple electrodes do is to start the process over again at half-way through the cycle, which is done exactly because it is widely recognized that the propagation of the causative electric pulse is often messed up as early as half-way throughout the sequence! This starting over, a kind of marriage therapy of the heart's contracting muscles, is less than what is desirable, and can be made better with a positive control through the electric pulse propagation process—which is the objective of the device disclosed in this patent application document.

Such multiple electrodes used in resynchronization therapy, usually, though not consistently, worked better than a single electrode. Yet, this lack of optimization of the heart muscle contraction has been a major problem known to the practitioners of the art. This uncontrolled propagation was shared by most, if not all models and their variations, in spite of the fact that the cardiologists were aware that uncontrolled electric pulse propagation caused inefficient heart pumping. Cardiologists knew that they had to address the problem of electric pulse propagation through the heart, but they have so far not succeeded in this goal. It has been a known problem in heart pacemakers, yet and amazingly, a problem which has defied solution for decades.

Moreover, even if multiple stimulating tips caused an improvement of the pumping squeezing sequence and efficiency, it had the detrimental effect of causing more muscle damage, as each anchored wire tip is a foreign body in the heart, also a foreign body which by necessity caused an injure to it, an injury which resulted in a scar tissue, which in turn has different electrical conductivity when compared with the normal heart, creating a problem spot for the very objective of controlled electric pulse propagation. Another problem was that, since often times the first attempt to anchor the tip in the endocardio is unsuccessful, either for mechanical or for electrical reasons, for every unsuccessful attempt the surgeon has to retract the tip then screw it again somewhere else, and occasionally even more than two attempts, each tip were usually responsible for multiple scars in the inner heart, which in turn posed limits to any dream of using a multiplicity of stimulating tips.

It seems that all prior art attempted to solve the problem of electric pulse propagation inside the heart muscle tissues with the use of multiple electrodes, while nobody succeeded to control the current propagation, in direction and magnitude, using one single electrode. Nor have prior art made full use of multiple electrodes to more completely shape the electric field within the heart muscle—which is the same as the electrical current path, because the electric field lines are the same as the force lines, or the lines along which the injected charges move.

Prior art simply used an arbitrarily shaped stimulating electrode, which than created a non-controlled electric field in the surrounding space, which in turn guided the injected charges (or electric current). Our invention offers a method and a means to adjust the electric field, independently from the stimulating electrodes, to the best shape depending on the particular case, as needed.

Several authors have discussed the problem of guiding the electric charge injected in animal tissue for electrical stimulation [e.g., Butson and McIntyre "Current steering to control the volume of tissue activated during deep brain stimulation", *Brain stimulation* V. 1, pg. 7-15 (2008), Butson and McIntyre "Role of electrode design on the volume of tissue activated during deep brain stimulation" *J. Neural Eng.* V3 pg 1-8 (2006), Julia Buhlmann et al. "Modeling of a segmented electrode for desynchronizing deep brain stimulation" *Frontier in Neuroeng.* V 4, article 15 (December 2011)]. These and others propose to take advantage of the electric field created by the stimulating electrodes to "guide" the electric charges injected by the same electrodes. An vivid analogy of the situation is the motion of the water along any river, which follows the channels that are directed to the ocean. In the case of the rivers the water is following the lines of the gravitational potential created by the planed earth underneath the path, while in the case of body cells electric stimulation the electric charges have to follow the electric potential created by any other electric charge that exist around the space in question. Of course that the stimulating electrodes by necessity create an electric field in the space surrounding them, which, in turn, cause a force on the electric charges injected by them, thereby applying a force, that is, guiding the path of the injected charges. What all the workers have so far failed to notice is that as long as they use the same electrodes for injecting charges and for electric field shaping they run into a brick wall because the charge injecting electrodes are on for a very very short time (a very small duty cycle), which typically may be 2% for DBS as used for Parkinson's Disease control or even <<1% for artificial heart pacemaking. Once one takes notice of this, it follows that a solution for the goal of guiding the charges AFTER they have been injecting have to rely on electrodes that do not inject charges into the system. A solution to this conundrum was offered by the inventor and co-inventors, as described in U.S. Pat. No. 8,954,145, Feb. 10, 2015, where we disclosed a second type of electrode, which we called then PASSIVE ELECTRODE, sometimes referred by us as field-shaping electrode. As defined by us, passive electrodes/ E-field electrodes are electrodes that are unable to inject electric charges because they are covered by an electrically insulating layer.

Patent application Ser. No. 15/019,969 (currently allowed, not yet issued, will issue November 2018) disclosed an improvement on the device disclosed in U.S. Pat. No. 8,954,145. Patent Ser. No. 15/019,969 discloses electrodes under the surface of the supporting structure Supp, which allows for more space for both the active electrodes and the passive electrodes as well. In this current patent application we disclose a further improvement on the E-electrodes/passive electrodes, consisting of a device and a method of enveloping or partly enveloping the target organ in a surface populated with the E-electrodes that control the current path as the ions move through the target volume. The guiding principle for this is that with more passive electrodes at different positions around the target volume, it is possible to better control the E-field in the target volume—there are more options, and therefore to better control the position, in space and time, of the propagating ions, because the E-field is the origin of the force on the ions.

OBJECTS AND ADVANTAGES

Accordingly, several objects and advantages of our invention are one or more of the following. A masking of the afferent neurons capability of carrying the pain information to the CPU housed at the skull of the person undergoing a procedure to extract cells suspected of being cancerous, for later biopsy. For example, the extraction of cells from the breast of a woman suspected of having breast cancer.

Another object and advantage of our invention is a better squeezing sequence of the heart muscle, starting the muscle contraction from the distal end of the heart further away from the exit port, to the proximal end of the heart closer to the exit port, with view to achieve a more efficient pumping, when compared with prior art heart pacemakers which were designed with no view to optimize the squeezing sequence.

Another object and advantage of our invention is to offer the ability to inject an electric current in the heart which causes a higher pumping fraction, or the fraction of the blood which is actually pumped out of it, or out of each chamber, when compared with prior art artificial pacemakers.

Another object and advantage of our invention is to adjust the electric field over the heart muscle to take better advantage of the atrial ventricular node to cause a better squeezing sequence of the heart muscle when compared with prior art artificial pacemakers.

Another object and advantage of our invention is to adjust the electric field over the part of the heart muscle where the His bundle and the right and left bundles are, to control the propagation times of the electric current coming from the atrial-ventricular node to the bottom and sides of the ventricle, to cause a better squeezing sequence of the heart muscle when compared with prior art artificial pacemakers.

Another object and advantage of our invention is to control the electric field where the Purkinje fibers are located, to take better advantage of the Purkinje fibers to cause a better squeezing sequence of the heart muscle when compared with prior art artificial pacemakers.

Another object and advantage of our invention are a better volumetric fit of the neural electrical stimulation to the optimal heart and/or other tissues target volume, when compared with current art heart, stimulation devices.

Another object and advantage of our invention is to better control the electric field around the supporting structure Supp from where electrical stimulation is injected in the target volume of the brain when performing Deep Brain Stimulation, to cause that the electrical stimulation reaches a larger volume of the target volume while better avoiding stimulating other parts of the brain that are near but outside and beyond the target volume.

Another object and advantage of our invention is the possibility of time control of stimulation sequences in neural stimulation, which is not achieved with current art devices.

Another object and advantage of our invention is a better control of the shape of the volume of neurons that receive electrical stimulation in brain stimulation, as in DBS (Deep Brain Stimulation) Another object and advantage of our invention is a better control of the shape of the volume of neurons that receive electrical stimulation in neural stimulation, as for TENS (Tanscutaneous Electrical Neural Stimulation) pain control in painful persons.

Another object and advantage of our invention is a better control of the shape of the superficial distribution of neurons as for pain control in TENS (Transcutaneous Electrical Neural Stimulation) devices, Another object and advantage of our invention is a better control and shape of the mostly locally planar electrical stimulation of neurons as used in some cortical brain stimulation. For this, planar but deformable sheets (similar to a bed sheet) are used, to conform to a 2-dimensional surface embedded in a 3-dimensional space.

Another object and advantage of our invention is to pay off the mortgages of the inventors.

If one or more of the cited objectives is not achieved in a particular case, any one of the remaining objectives should be considered enough for the patent disclosure to stand, as these objectives and advantages are independent of each other.

Further objects and advantages of my invention will become apparent from a consideration of the drawings, the summary, the description of the invention and its variations, and the claims.

SUMMARY

It is well known in cardiology that the heart pumping efficiency is a direct consequence of a proper propagation, in time and space, through all 3-dimensional available electrical paths in the heart cells, of the electrical pulse that causes the heart contraction, including the contraction sequence. The fact that the electrical path in the heart is a 3-dimensional quasi-continuous current distribution is not as ingrained in the conscientiousness of most workers in the field as I wish it would. This 3-dimensional current propagation is acknowledged to be true whether the electrical pulse is the natural one starting at the SAN (sino-atrial node)

or an artificial one, starting at the anchoring position of an artificial heart pacemaker. It is interesting to note here that evolution does not, and in fact cannot progress along modifications on the heart design toward the most efficient possible pumping, but only to the most efficient pumping from the existing configuration—which may well be incompatible with the best solution. It follows from this it is not true that the heart that has been evolved by natural selection is the best solution—and in the case of the heart contraction it is not the most efficient pumping. Moreover, even if nature had evolved the best possible contraction sequence, the artificial heart pacemaker does not inject the electric current at the same location as the natural pacemakers, and consequently the artificial heart pacemaker should correct for this variation. Finally, due to the asymmetry of the heart muscle, it would be expectable that the best electrode would include some asymmetry, as required to provide the best current density around the heart. Consequently, what is needed is a heart pacemaker that could maximize the pumping efficiency, not a pacemaker that just makes the heart to pump; just make the heart to pump is old, we need to do more now, and it is possible to do more, as we describe in this patent application. Such a goal of maximizing the heart pumping capabilities has eluded the practitioners because of a lack of mechanism for precise control of the current injection, in position, direction and relative timing, of the electrical stimulation. Our invention is a step in the direction of better control of this stimulating pulse. Our invention discloses a mechanism to control the magnitude and the direction of the initial current injection in the heart muscle, also time delays between current injected from different locations on the surface of the stimulator; in other words, our invention affords the possibility of controlling the vector current, and the relative time at different directions and places, as opposed to only its magnitude, as in prior art. Our invention also applies to other electrical stimulations as brain (DBS and cortical stimulation), spine, skin, cochlea and others.

DRAWINGS

FIG. 1—A schematic view of a heart.

FIG. 2.—A schematic view of a heart with two implanted electrodes and also extra field-shaping electrodes of our invention.

FIG. 3—A schematic view of a heart stimulator.

FIG. 4—a schematic view of the stimulator of our invention showing field-shaping electrodes 140_t2 of our invention underneath old-style active electrodes 140_t1.

FIG. 5.—A possible implementation of our invention with field-shaping electrodes at the surface only.

FIG. 6—a schematic representation of our invention.

FIG. 7—a schematic representation of a cordum of our invention.

FIG. 8A—schematic representation of an atrium emptying into the ventricle.

FIG. 8B—schematic representation of an atrium emptying into the ventricle.

FIG. 8C—schematic representation of an atrium emptying into the ventricle.

FIG. 8D—schematic representation of an atrium emptying into the ventricle.

FIG. 9A—schematic representation of a ventricle emptying its blood.

FIG. 9B—schematic representation of a ventricle emptying its blood.

FIG. 9C—schematic representation of a ventricle emptying its blood.

FIG. 9D—schematic representation of a ventricle emptying its blood.

FIG. 10—is the gravitational field of the earth including its deviation due to a large mountain.

FIG. 15A shows a few possible electrode configuration for electrical stimulation.

DRAWINGS—LIST OF REFERENCE NUMERALS

BAT1=Battery and controlling electronics box, usually implanted in the patient's chest.
MP1=Microprocessor 1. One of the possible units capable of executing a programmable sequence of instructions, as the venerable 8085, or the 8086 (which was the brain of the first IBM-PC), 80286, 80386, 80487, pentium, DSP, microcontrollers, etc. Some of these may include memory, DAC, ADC, and interface devices.
100=body of picafina of our invention.
110=electrical energy storage unit (e.g., a battery)+microprocessor (MP1)+parallel-to-serial converter.
122=Serial address (may also include return ground, or may use the same return/ground as power 124).
123=reset line/control bits.
124=power conveying means.
130=ST1=electrical stimulating probe, in the main embodiment is screwed in the inner part of the heart, brain, or other organs. It is also named Ex when used as a sample extractor.
131=anchoring arms to prevent the heart stimulator type (piquita) from moving back once it is forced into the endocardio/miocardio.
132=main body of piquita heart pacemaker or the picafina DBS body called "lead" by Medtronic.
140-*t1*=type1 or active electrodes (standard electrodes, capable of injecting current in its neighborhood).
140-*t2*=type2 or field-shaping (passive) electrodes (electrically insulated electrodes, capable of influencing the electric field lines, but not capable to inject current). Typically type 2, field-shaping electrodes are covered by a silicon dioxide layer, but any other insulator is possible, the type of insulator being not important for our invention.
140_t3=underground field-shaping (passive) electrodes.
210=memory with local address for each electrode 140.
220=SW=switch to turn electrodes on/off.
230=comparator to determine if switch 220 should be turned on or off.
240=digital comparator/decoder.
250=enable bit for 260.
260=comparator/decoder for stimulator addresses.
307=tricuspid valve, between the right atrium and ventricle.
309=pulmonary valve, exit from the right ventricle.
310*atr*=atrium.
310*ventr*=ventricle.
410=hermetically sealed box containing the energy storage unit (battery), the microprocessor MP1, the serial-to-parallel converter and all the necessary electronics for the device to operate, as is used in prior art.
510=serial-to-parallel converter.
520=parallel lines for addresses (may also be used for control and data).
830=address decoders (AddDec)
Alphabetical Labels
A=digital, binary address lines.
AVN=Atrial-ventricular node.
B=power line (voltage or current source).
bl=blood level.
Ex=extractor, also labeled as 130
HB=His Bundle.
In=Injector, needle capable to inject medicine in the muscle of some unfortunate patient.
LBB=Left bundle branch.
LA=Left atrium.
LV=Left ventricle.
m=mountain (exaggerated height for display)
Nd=needle used for hypodermic injections
PA=protruding arm.
PF=Purkinje fibers.
RA=right atrium.
RBB=Right bundle brunch.
RV=Right ventricle.
SNA=sino-atrial node.
SW=also 220 and 810.

DETAILED DESCRIPTION

Overview

Figure 3:
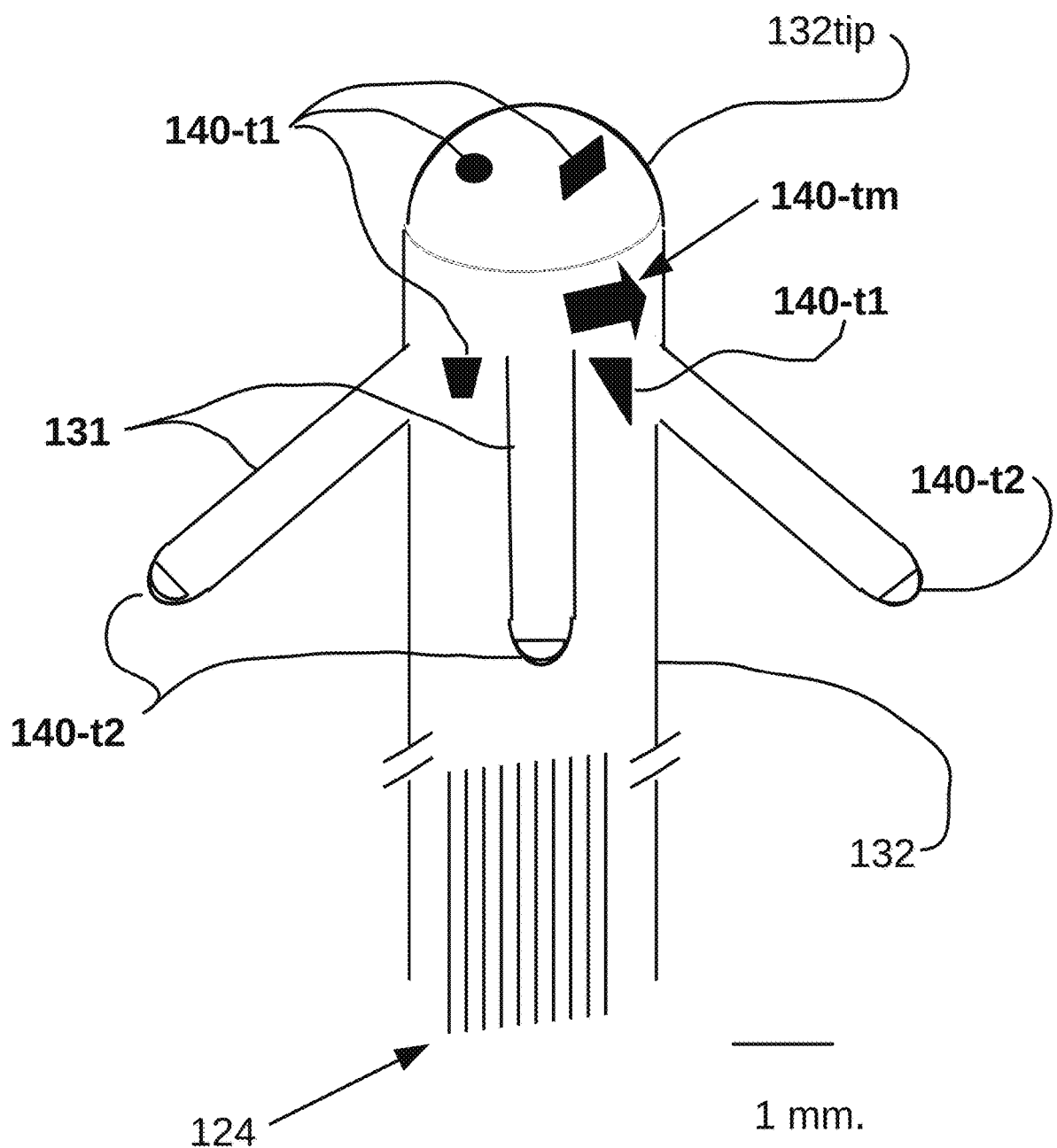

FIG. 3 shows the main elements of an existing heart pacemaker, which we call cordum. FIG. 3 shows one of the current art anchoring distal extremities 132*tip*. Note that different ending anchoring attachments 131 are in use, and that the model shown in FIG. 3 uses one of the several used attachment endings, but the same principles apply to other anchoring attachments. The main body 132 of the cordum device may have a diameter of 1-2 mm or less (approximate dimensions), and the smaller anchoring side arms 131 may have a diameter of 0.5-1 mm (approximate dimensions, the actual dimension being unimportant for the invention). Anchoring arms 131 should have such size and strength enough to keep the tip of the stimulating cordum structure 132 secured in place once it is inserted into the heart muscle. Anchoring arms 131 should prevent the cordum stimulating device from moving back, out or the muscle, this being one of the reasons for its shape and form, resembling a ship's anchor, which has the similar function of holding firm to the sand below the ship. These dimensions may vary without changing the nature of our invention and these values are given as a possible dimension only. On the surface of the main body 132 and of the smaller side arms 131 there are several electrodes, perhaps randomly-shaped, which are represented by either a solid black electrode or by the contour around a white electrode. The solid black odd-shaped patches 140-*t1* represent electrodes which we call active, or type-1 electrodes, and the open, odd-shaped patches 140-*t2* represent electrodes which we formerly called passive electrodes, but are now calling field shaping electrodes, or type-II or type-2 electrodes.

The field shaping electrodes have been disclosed in earlier patent applications of ours, e.g., patent application Ser. No. 13/470,275 (from now on Lee275) currently issued U.S. Pat. No. 8,954,145, and patent application Ser. No. 15/019,969 (from now on Lee969), currently allowed, to issue in November 2018, and this invention is a modification of the location of the field shaping electrodes, which are called passive electrodes in these earlier documents.

Figure 4:
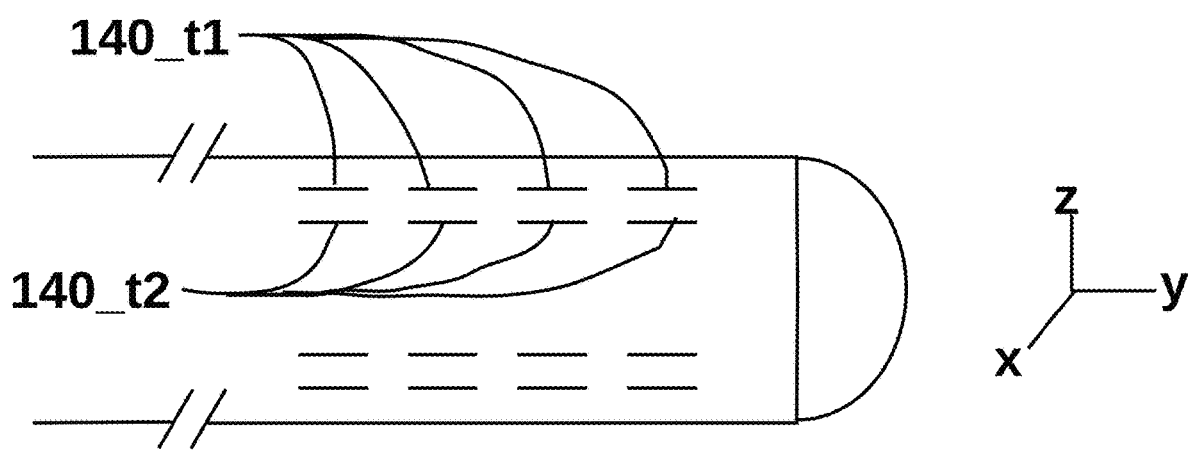

FIG. 4 shows another view of the sub-surface electrodes of our invention, showing the active electrodes at the surface and the field-shaping electrodes underneath the active electrodes. FIG. 4 is a cut-away displaying a cut parallel and containing the axis of a cylindrical supporting structure, with some electrodes 140_t2 below the surface and some electrodes 140-*t1* at the surface of the supporting structure.

Figure 5:
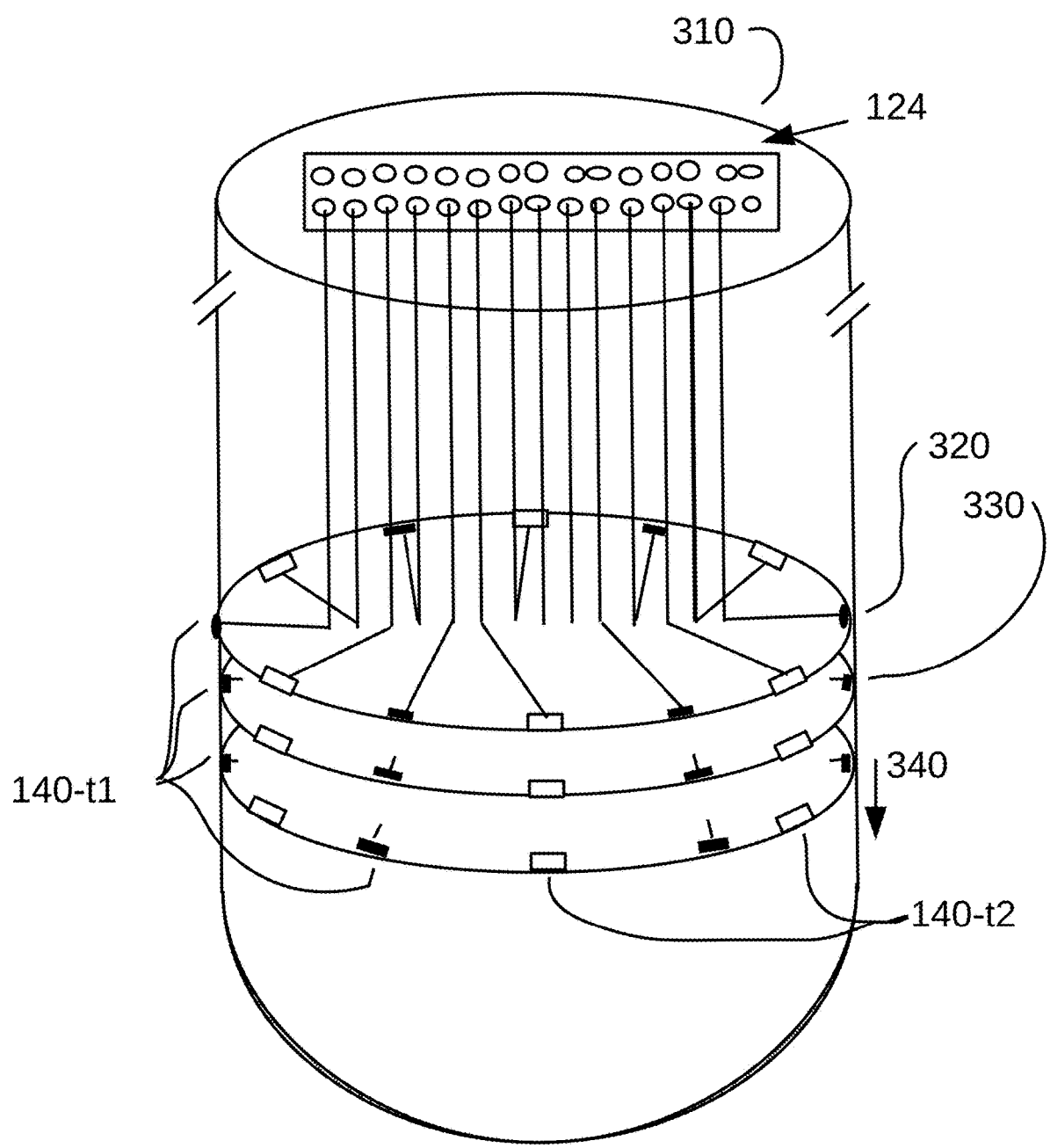

FIG. 5 is a perspective view but with electrodes only at the surface of the supporting structure. When 140_t2 are buried under the surface of the supporting structure Supp, all the surface electrodes may be active, which increase the surface available from which to inject current—as there is no need to put field-shaping electrodes on the surface. At the same time, the available surface for the field-shaping electrodes is also larger when they (the field-shaping electrodes) are buried—because, if the passive or field-shaping electrodes are buried under the surface of the supporting structure Supp, then they can use all the area just under the surface. The sub-surface or buried configuration increases the available surface for both active and field-shaping type of electrodes, causing an improvement on the device over previously described field-shaping electrodes.

FIG. 5 shows a perspective view of the brain-style (a.k.a. Picafina), with some wires down the length of the device, but not all wires to prevent cluttering the drawing. Only the wires that make the connection to the electrodes at the top layer 320 are shown. Other electrodes, on the layers below (330, 340, etc.), are also connected to dedicated wires, similar to the ones shown in this figure. In the main embodiment the wires are of the printed circuit type, but lose wires are also possible, though a smaller number of them would be possible. At the top of the brain-type picafina shown in FIG. 5 there is an electrical connector, which is capable of matching another connector with wires leading to the battery/controlling electronics implanted at another location, as in prior art.

Whether the device in question is a cordum (for the electrical stimulation of the heart), popularly known as an [electric] pacemaker, or a picafina, adapted to cause an electrical stimulation on certain parts of the brain, as the sub-thalamic nucleus, the globus pallidus interna, etc. they all have a common structure: a body, a battery or some other source of electrical energy, an electronic control unit, which usually, but not necessarily is a digital device, a supporting structure adapted to keep electrodes at a fixed position with respect to the animal, and wires connecting these elements. We call the combination of these parts as an electric stimulating assist system.

The field shaping electrodes of our invention may be located at the surface of the supporting structure Supp or under the surface of the supporting structure Supp. The possibility of locating the passive (or field-shaping electrodes) below the surface of the supporting structure Supp causes a most important improvement on the electrical stimulating device, which is that the whole surface of the supporting structure Supp can then be dedicated to the active electrodes, allowing more options for the electrical stimulation. The reader should note here that moving the passive electrodes to below the surface of the supporting structure Supp also increases the available positions for the passive electrodes, because the passive electrodes need not be sharing precious real estate with the active electrodes. Of course that the passive electrodes may also be located at the surface of the supporting structure Supp.

Once any passive electrode is connected to the battery and controlling electronics by electrically conducting wires, the electric potential of the electrodes can be varied according to the instructions saved in the memory of the controlling electronics, which in turn determine the value (and signal) of the electric charge stored (forced) in the electrodes; call this charge q. Elementary physics then shows that this electric charge q can contribute to the value of the electric field in the space surrounding the electrode supporting structure Supp. Moreover, the electric field, and therefore the force on electric charges propagating in the volume in question is determined by the formula:

$E$-vector$=[k*(q1)/d^{**}2]*r$-hat $F$-vector$=q2*E$-vector where E-vector, F-vector, etc. (also E-field, F-field, which is the same because the field in question is a vector field) indicate that the quantity in question is a vector, and r-hat indicates a unit vector with that name, which, in this case is along the line connecting the two charges q1 (which is originating the electric field, and q2, which is under the influence of q1, or under the influence of the electric field created by q1, and the force F-vector is the force that acts on q2. The common notation is to make E-field, F-field, etc. in boldface, which may not be available at the USPTO press, so we avoid the bold face use convention. This force F-vector has to be determined beforehand (that is, calculated), to be such as to cause such a force on the propagating electric charges, usually in the forms of ions, that these electric charges stay on a desired volume (in the DBS brain case) and also, in the case of the heart, propagate at such a speed along the heart muscle that the muscle contraction causes as complete a pumping as feasible—given the poor design of the heart by the intelligent designer. In general the passive electrodes should be set at such an electric potential that the electric charges propagate within a desired velocity (speed and direction) that the electric charges stay within a desired volume.

Active, or type-1 electrodes 140-$t1$ have a metallic surface (or other electrically conducting surface) which is capable of conducting electricity. Other than their smaller sizes and odd-shapes, they correspond to the prior-art electrodes for electrical stimulation of the heart, brain, and other body parts, from which they only differ in shape and size but otherwise being electrically and functionally similar—though their size and configuration add to their functionality, as explained below. Field-shaping, or passive, or type-2 electrodes 140-$t2$ (all equivalent names for the same element) also have a metallic surface, but their metallic surface is covered by an insulating layer, which may be made of silicon oxide but other materials are also possible. Field-shaping, or type-2 electrodes are unable to inject current into the surrounding tissues, but when set at fixed electric potentials (voltages). The field-shaping electrodes change the shape of the electric field in the neighborhood of the cordum, therefore changing the paths of the injected currents. Field-shaping (type-2) electrodes are incorporated in the cordum for the purpose of shaping the electric field configuration (to change the spatial configuration of the surrounding electric field which in turn changes the path of the electrical stimulation).

Figure 16:
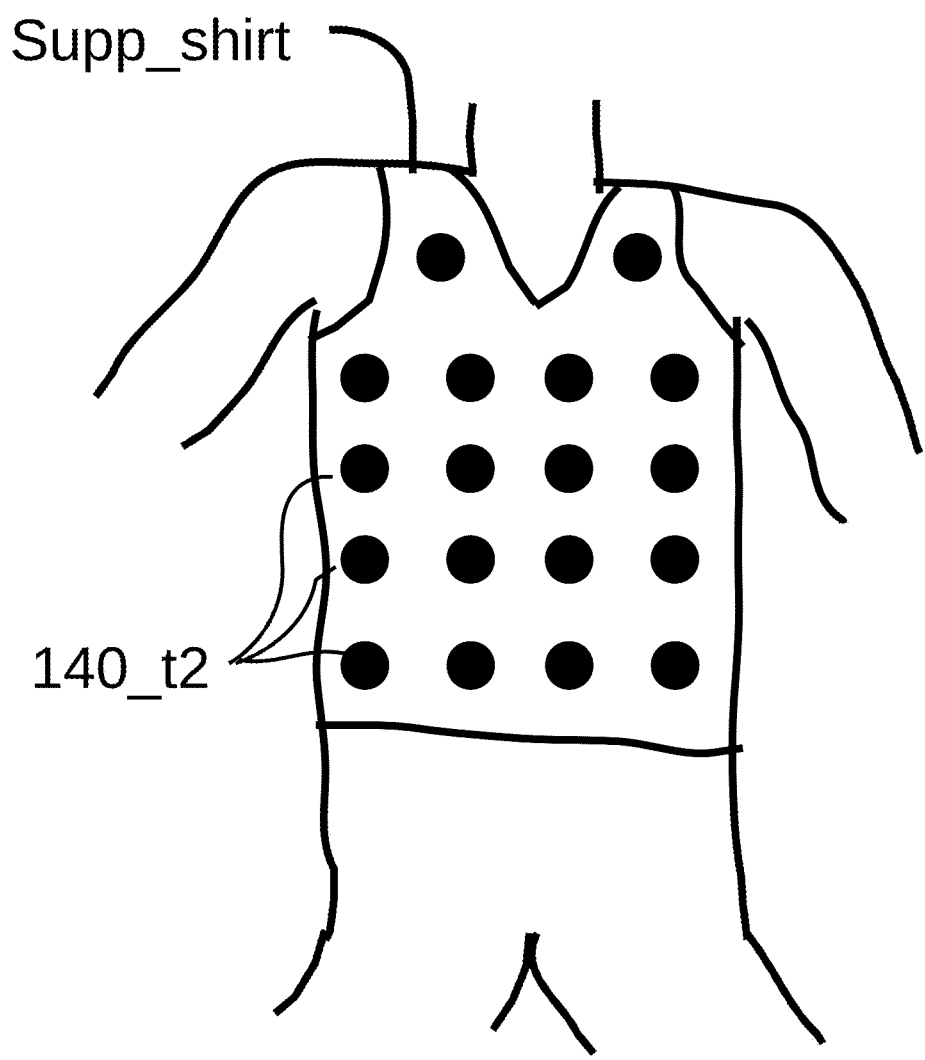
FIG. 16 shows a number of passive electrodes 140_t2 distributed on a wearable shirt-like support Supp_shirt. The fractional surface coverage could be of the order of 75%, which is the approximate solid angle coverage offered by the shirt's front+back+sides.
Figure 17:
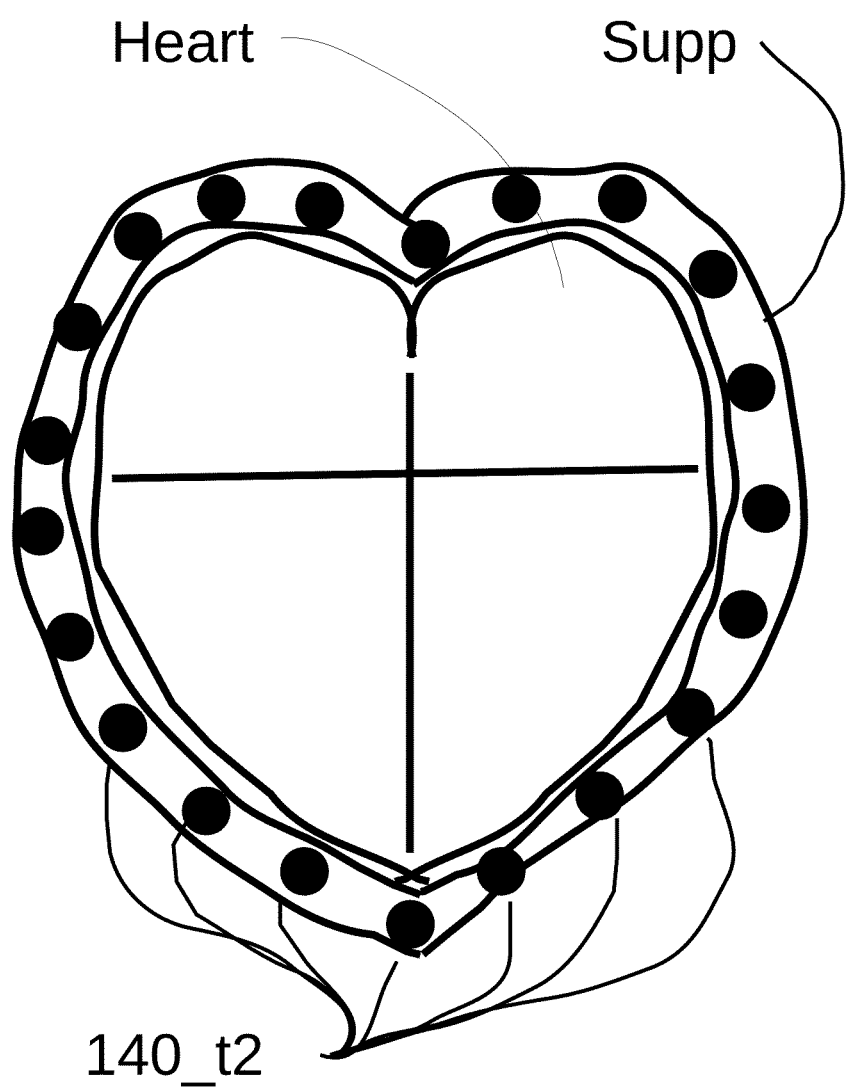
FIG. 17 shows passive electrodes 140_t2 distributed on a membrane surrounding the pericardio.

We want to anticipate here to the reader that the passive electrodes may be anywhere in the patient: the passive electrodes may be near the active electrodes, they may be near or far from the target volume (the volume that is electrically stimulated), the passive electrodes may be wrapped around, covering partly of or totally the target volume, as schematically shown in FIG. 17, where one sees a surface covering a heart, see also references (1), (2) and (3), they may be on the wires that connect the battery to the electrodes, they may be on any supporting structure elsewhere in the patient, which may be designed especially for the purpose of holding the passive electrodes in fixed position with respect to the patient, and among these supporting structures elsewhere in the patient, some may be implanted under the skin of the patient, others may be attached to the skin of the patient, but on the outside of the skin, others may be worn outside the patient, as passive electrodes attached to a shirt (see FIG. 16), or to a hat (see FIG. 18), or to a belt (see FIG. 19), etc. An example of a supporting structure Supp wrapped around a target volume is seen at FIG. 17. In this FIG. 17 one can see a schematic representation of passive electrodes 140_t2 distributed on a membrane surrounding the pericardio. Such a membrane was developed, fabricated and actually used on a rabbit's heart ex-vivo (ref. 1, 2, 3). In this case the membrane around the rabbit's pericardium was populated with data collecting sensors, as pressure sensors, electrical reading electrodes, pH sensors, etc., and they took the heart out of the unfortunate rabbit, then kept it beating with a heart pacemaker and a heart-lung machine while making the physical measurements. Our device would have passive electrodes on the membrane instead, so it is a simple modification of an existing technology. Another difference between our work and the work of LizhiXu et al. referenced above is that we will murder no rabbit.

Figure 18:
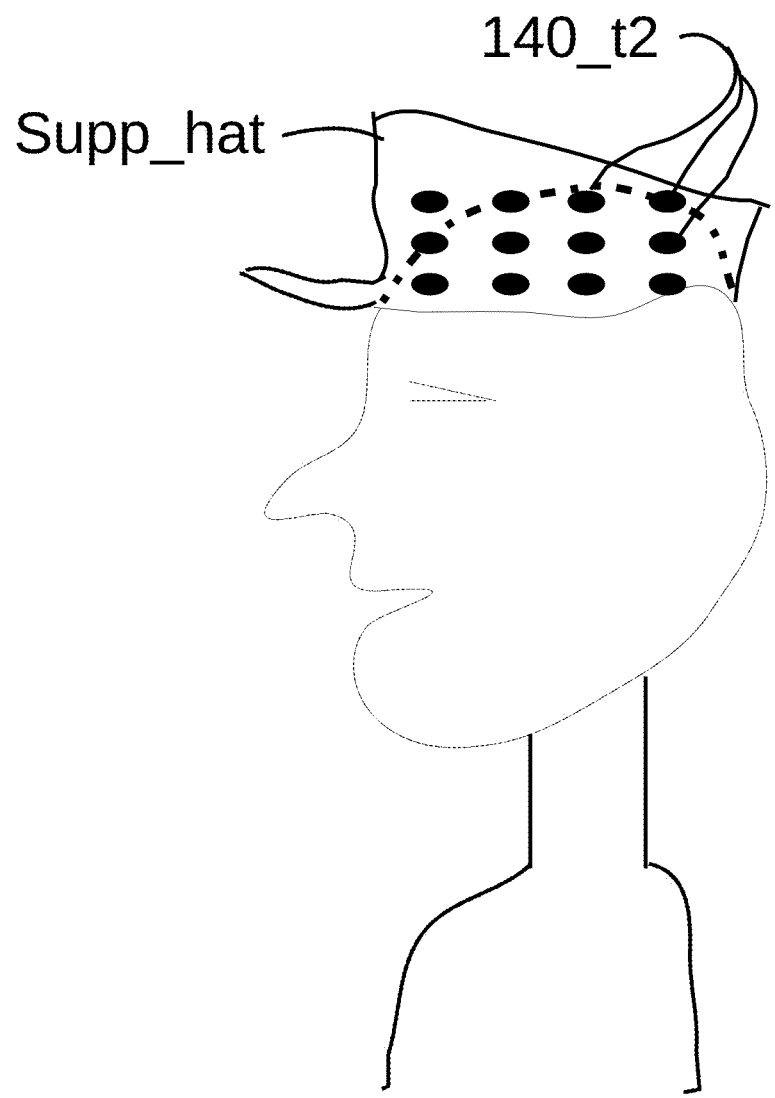
FIG. 18 shows a number of passive electrodes 140_t2 distributed on a hat-like support Supp_hat. The fractional surface coverage could be of the order of 60%, which is the approximate solid angle coverage offered by the hat's front+back+sides+top.

FIG. 18 displays a similar device, this time supported by a hat, a supporting structure Supp called Supp_hat. Supp_hat has passive electrodes 140_t2 around the hat, which create an electric field E-vector in the volume of the head of the patient, useful for DBS, cortical stimulation, etc. In the case of the FIG. 18 the hat is of the type of a baseball hat, but this particular style is not the only one, any hat-like structure being equivalent, as the type of hat does not matter. Instead of a hat the same objective can be achieved with a bandana, or similar fashion devices, as long as it is a supporting structure in fixed position with respect to the head (and brain) of the wearer.

Figure 19:
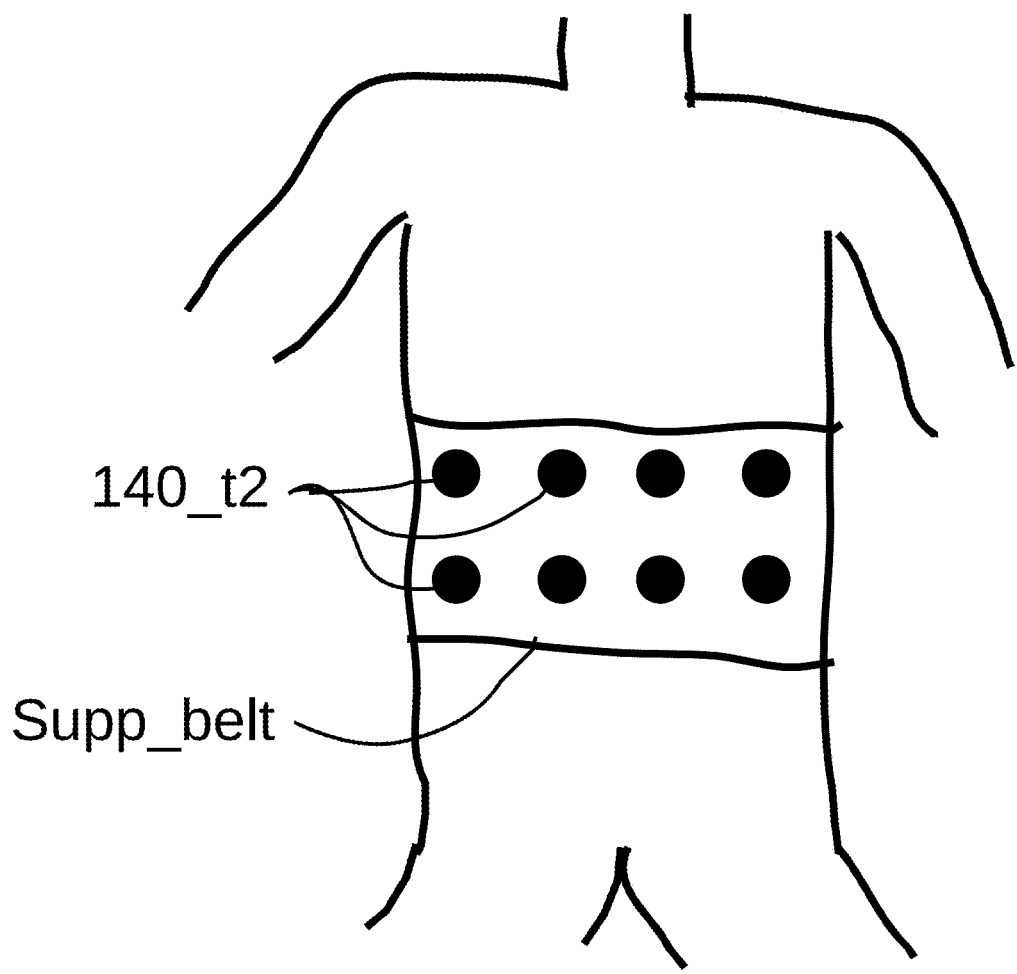
FIG. 19 shows a number of passive electrodes 140_t2 distributed on a wearable belt-like support Supp_belt. The fractional surface coverage could be of the order of 50%, which is the approximate solid angle coverage offered by the a wide belt around the abdomen of the patient.

FIG. 19 displays another similar device, this time supported by a belt (Supp_belt), a wide belt of the type used by persons lifting heavy loads for either work or for sports. In this figure one can see a number of passive electrodes 140_t2 that are suitable to create an electric field E-vector in the belly of the wearer, perhaps to help some stomach electric stimulation, as for appetite control or some other objective. In this case shown at FIG. 19 the belt Supp_belt is wide, as is the belt to protect people from possible damage caused by lifting heavy objects, but the belt may also be narrow, say, 3-6 cm (1-2 inches), as are the normal belts used to keep the pants in place, only that a narrower belt would have less effect than a wider belt as shown. But the width of the belt does not change the nature of having a supporting structure at the abdomen of the patient that is receiving electrical stimulation.

In this patent application we suggest passive electrodes on the wires that go from the batteries to the electrodes themselves, and also on other supporting structures especially designed as a support for the passive electrodes, as described elsewhere in this patent application, as shirts (FIG. 16), hats (FIG. 18), belts (FIG. 19), (outside the patient) and on other supporting structures wrapped around some organ (FIG. 17), etc. In fact there are an infinite number of locations for the passive electrodes, which are covered by variations of the supporting structures disclosed on this patent application. These supporting structures may wrap around the heart, the chest or parts of the heart or part of the chest of the animal, or the supporting structures may wrap around the brain, the head or parts of the brain or parts of the head of the animal, or the supporting structure may wrap around the stomach, the abdomen or parts of the stomach or parts of the abdomen of the animal or of the patient.

To physically achieve the above description, the controlling mechanism, in this case a microcontroller MC1 residing in the battery/control unit 110 (FIG. 6), is loaded with a program (or software), which is capable of executing automatic repetitive tasks following a programmed sequence the details of which are adjusted by a medical professional or by the patient himself, which determines a particular combination of active and field-shaping electrodes to use, also able to determine which electrodes of each type to use, also able to send this information by wires to the stimulating unit 132.

The correct sequence can be determined, for example, by the examination of an EKG (Electro Cardiogram) while varying the active electrodes of each type, their electric potential (voltages) and relative time sequence. Microprocessor MP1, located in box 110, select which wires 124 to be connected to electric power and the electric potential (voltage) level as well, which may be different at each wire 124. Each were 124 connects to one of the electrodes 140-t1 or 140-t2. Each electrode type can be turned on or off (connected or disconnected from the electrical power) under the control of microprocessor MP1.

Figure 6:
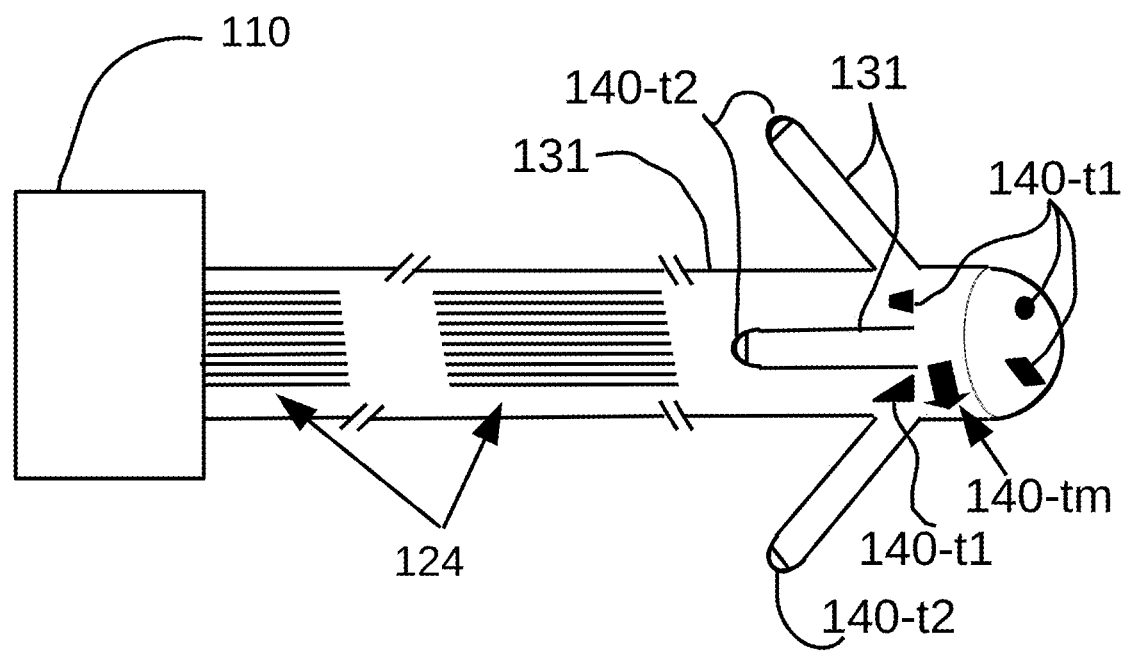

The invention also discloses an important marker to determine the angular position of the cordum (or picafina for the brain, or other equivalent device for other organs, neurons, etc.) with respect to the heart (or brain, organ, etc.) in which it is implanted. FIGS. 3 and 6 show one such possible marker: a type-1 active electrode 140-tm with such an X-ray opacity (absorption) to be visible during the fluoroscopic images taken during electrode implantation as normally done. Other markers are possible for the same purpose, as the same shapes on type-2 field-shaping electrodes, as side arms 131 of different lengths and/or diameters, or any other asymmetric feature that is visible in some sort of imaging technique, as MRI, X-ray, ultrasound, etc. It is part of our invention that each electrode position and size and orientation is known to the cardiologist (and the computer which he will use to program the device), each electrode being know by a designator, as a number, as 1, 2, 3, . . . etc., or any other alphabetical or numerical pattern or any other naming system as desired. Marker 140-tm allows for the computer program to know the angular position of each electrode, which is needed to determine which individual electrode to connect to which electric potential (voltage), according to their actual position within the heart muscle, as the cordum happened to have been anchored in it.

Inside the main body 132 and the side arms 131 of the cordum supporting structure, there are wires 124 extending from the controlling electronics, microprocessor and battery to each electrode 140 (of either type, t1 or t2). Wires 124 may be either standard wires or may also be printed wires, as in printed circuit boards. The technology of printed circuits is a well advanced technology with many methods to print the wires, and the wire manufacturing is not part of this invention, as any of the existing technologies are acceptable to implement the invention.

The main embodiment uses 10 wires from the battery pack/control unit 110 to the cordum supporting unit 132, which are connected to the 10 available electrodes 140 by the 10 wires 124—one wire for each electrode 140. This particular choice of 10 wires and 10 electrodes should not be taken as a limitation on the invention, because more wires and electrodes, or less wires and electrodes are possible still within the scope of the invention, as obvious to people familiar with the art of electronics. It is also possible to connect the ground (or return) wire to any number of electrodes (or pads), both type-1 and type-2

Figure 7:
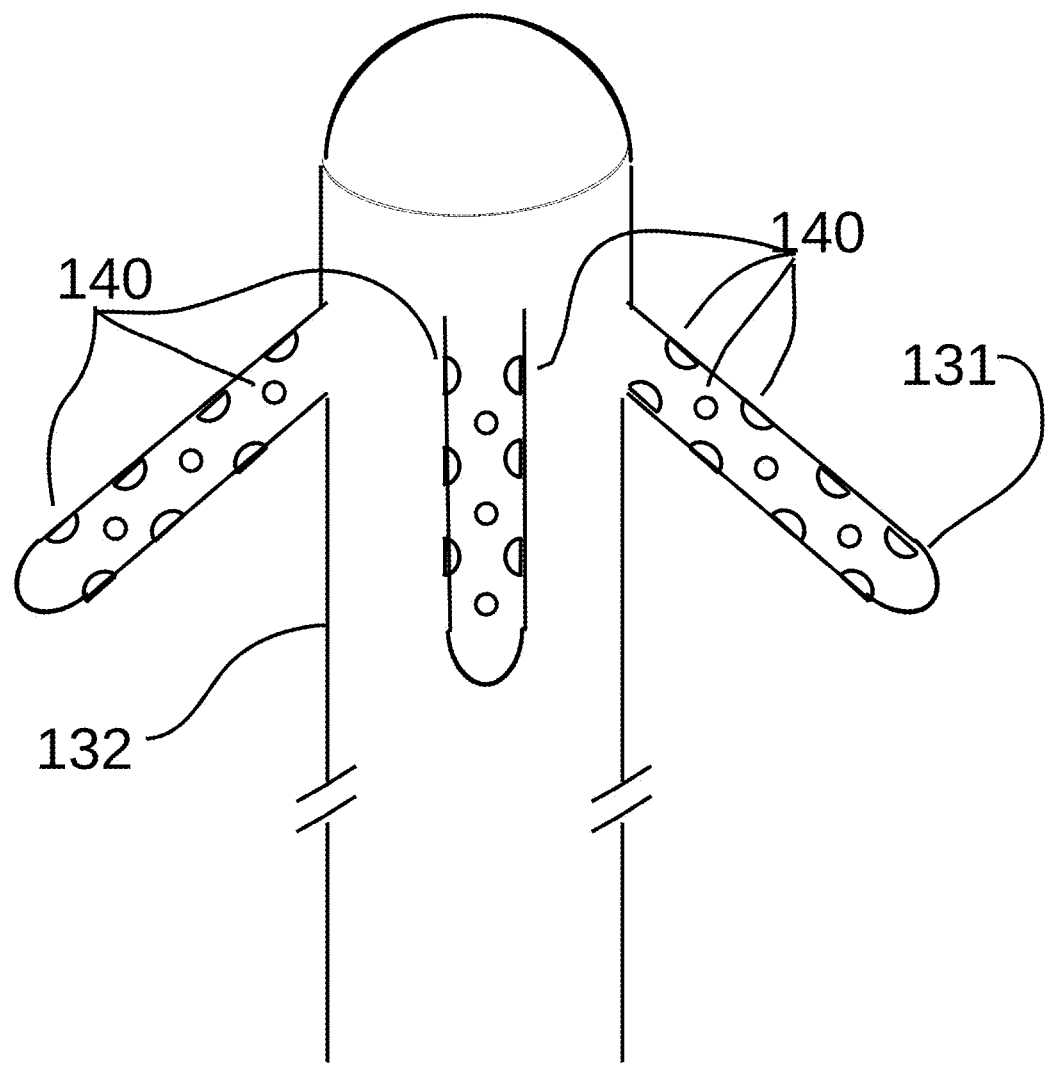
Figures 8A, 8B, 8C, 8D:
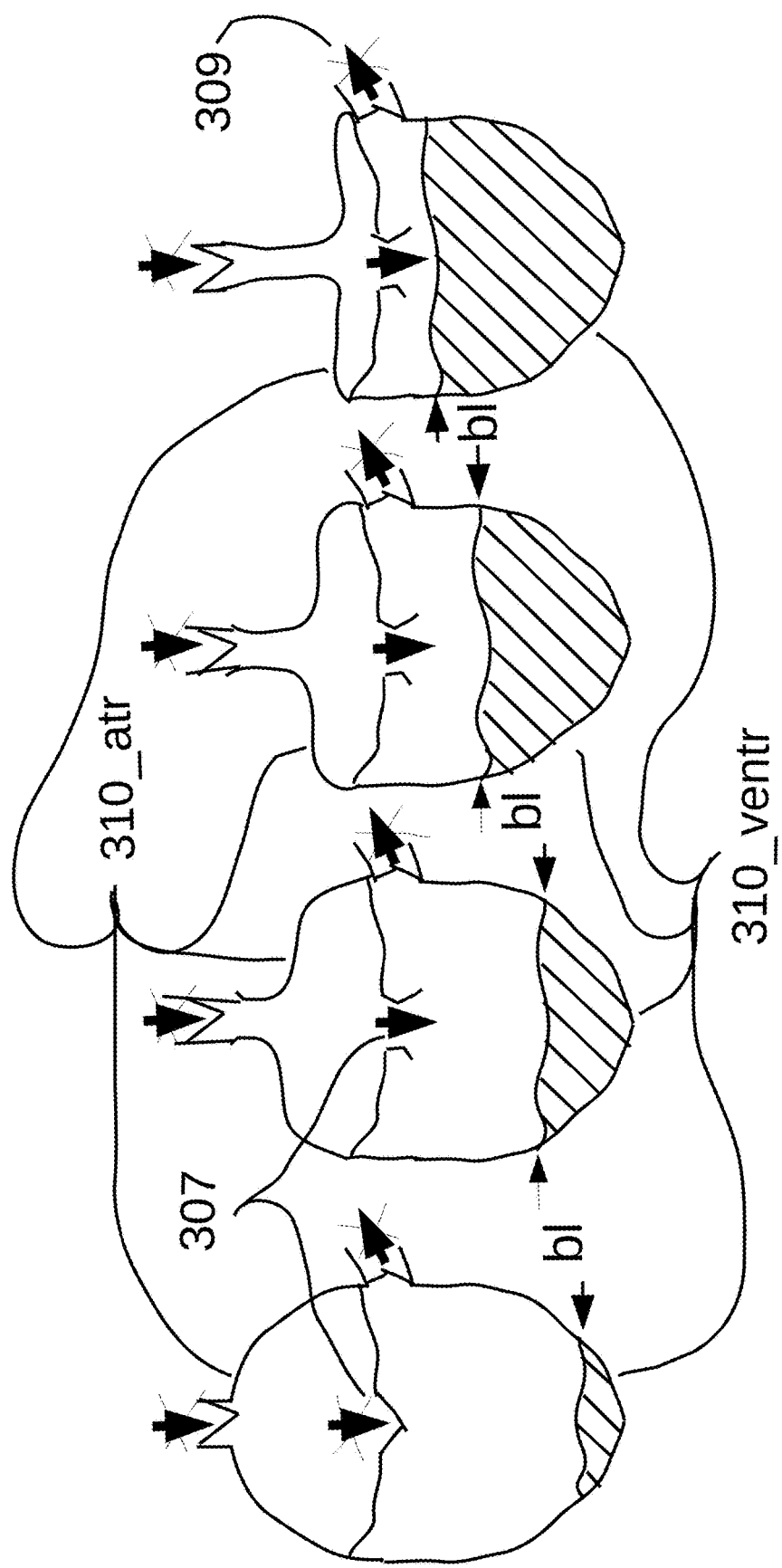

The random placement, shape and size of the electrodes is a distinct feature of our invention, as it contributes for the creation of a spatial asymmetry of the electrodes, which in turn causes an asymmetry in the spatial distribution of the injected current, either its magnitude or its direction. Careful selection of which electrodes to turn on, and at which electric potentials (voltages) can create the most desirable electric field shape on the volume of the heart. A careful selection of which electrodes is able to produce a better resulting stimulation which is suited to the asymmetric heart muscle 3-dimensional shape and causes a more complete squeezing sequence and better ejection fraction (the fraction of blood sent out of the heart). It is to be noted that if any symmetry is required, our invention is backwards compatible, being able to reproduce old art stimulating surfaces as a particular case of an arbitrary shaped surface. Note that if a symmetry of current magnitude and direction is desired, it can still be achieved within a reasonable accuracy, by the appropriate selection of a number of electrodes which, as a set, defines the desired symmetry. Naturally the degree of symmetry possible to be achieved depends on the number of electrodes available: more asymmetry with more electrodes (that is, more complex electric fields with more electrodes) FIG. 7 shows a variation of the heart-type stimulator cordum with electrodes only at the surface of the side or anchoring arms 131. For simplicity this figure does not differentiate between the two types of electrodes 140-t1 and 140-t2, but it is understood that the general denomination 140 intends for both types of electrodes, either randomly or orderly distributed on the surface of 131.

The improvement of the invention is to bury at least some, potentially all the field shaping electrodes under the surface of the supporting structure 131 and 132. With this geometry the full surface of the supporting structure 132 and 131 is available for the active, or electric current injecting electrodes, which in turn increases the possibilities for controlling the 3-dimensional current through the heart—or through the brain in DBS, or through another organ, or another nerve, etc. The buried electrode, which we also call subterranean electrode, functions in the same way as the passive electrodes disclosed in the previous inventions (Lee275 and Lee275 and Lee969) but add functionality to them because more surface becomes available for the active electrodes and also, more important, the field shaping electrodes have more control on the electric field because they form a more continuous surface enclosing the volume inside, as predicted by the Lara conjecture, which, in the weakest form, states that it is possible to create an electric field that is almost the same as any desired electric field in any volume V that is completely enclosed by a surface $S_{c1}$ provided that one has strong control on the electric charges on most of the surface of $S_{c1}$. With an eye on the Lara conjecture, we propose another improvement on the supporting structure for the buried or subterranean electrodes, the improvement consisting on a supporting structure that allows buried electrodes at a surface that almost completely encloses the target volume. For example, for the heart pacemaker the enclosing supporting structure could be a sac sutured on the outer surface of the heart, just outside and beyond the pericardium, as shown schematically at FIG. 17. Such a sac has been used ex-vivo on the heart of a poor rabbit (without his consent, the inventor believes), as described at references 1, 2 and 3. Such a surface would require a few holes for the arteries and veins in and out of the heart, but it could enclose 90% of the heart (or, in other words, the holes for the arteries and veins would be less than 10% of the total surface. Or perhaps less than 90%, as only 70% or even 50% of the imaginary surface enclosing the heart just beyond the pericardium Or such a surface around the heart could be a shirt with the buried or subterranean electrodes on it that could be worn by the patient, as shown in FIG. 16. Such a shirt would cover perhaps 60% to 70% of the surface around the heart, which is a small fraction of an enclosing surface, but it would have two major advantages over the surface right on the outer surface of the heart that (1) it would require no surgeries and (2) the batteries could be changed easily, which is not the case for the implanted surface on the pericardium. Advantage number 1 above would be good for the patient but bad for the surgeon, so it would not satisfy all parties, but this should not be an argument against the device we disclose here.

Alternatively, this external surface holding passive electrodes at its surface or below its surface could be smaller than a shirt, as a belt, perhaps a wide belt similar to the belts used to hold the belly of a person who is lifting weights, as for working, as shown at FIG. 19 but it could be narrower too, even of the width of a standard pants belt, as 2 to 5 cm (1 to 2 inches). Such a belt could be useful for electrical stimulation of the stomach, as for appetite control.

In general terms, any of the variations for the heart pacemaker that wraps around the heart or parts of the heart, or the chest or parts of the chest of the animal, or the head or parts of the head of the animal.

Another type of electrical stimulation that is becoming more common is for the stomach, etc., for appetite control and other uses. Such an electrical stimulator could wrap around the stomach or parts of the stomach, or the belly or parts of the belly of the animal.

For the brain, such an enclosing surface could be a malleable surface either just below the skin at the head or under the cranium. The former case (below the skin) would be easier to implant than the latter case (under the cranium). Such a surface would not completely enclose the brain either, but it would be capable of having a strong effect on the electric charges propagating in the brain. On one embodiment the almost-enclosing surface would have a hole at the bottom for the neurons to pass into the spine, with other holes for the neurons that bring in the visual input, the aural input, etc. On another embodiment, given that the hole at the bottom of the brain would have the largest diameter, when compared with the hole for the visual input, aural input, etc., the neurons leading to the spinal cord could be severed, obviating the need for this larger hole. Given that the brain is so rarely used by most people, this severing of the connections to the spinal cord would cause no discernible effect on most people.

Or, similarly to the shirt with underground electrodes for heart pacemaking applications, an external surface to support passive electrodes for brain stimulation (as in DBS) could take the shape of a hat worn by the patient taking any of the common types of hats, from a cowboy hat to a baseball cap, or other types, as shown at FIG. 18. Such a hat could also have an extension at the back of the head, of the type used to block the sunlight from the back of the neck, used by many working people, and/or an extension around the neck, of the type used as scarf in cold places. Both the extension at the back of the head and the extension of the type used as scarf would increase the surface area from where passive electrodes could create an electric field inside the head, which would increase the strength of the device. As the reader can see, many variations are possible, with the supporting structure both implanted near or just around the target volume, and external to the body as well.

As the reader can see, there are many variations of the brain pacemaker (as for DBS) that wraps around the brain or parts of the brain, the head or parts of the head of the animal.

Operation of Invention

Background Information on Operation of the Invention.

Figure 1:
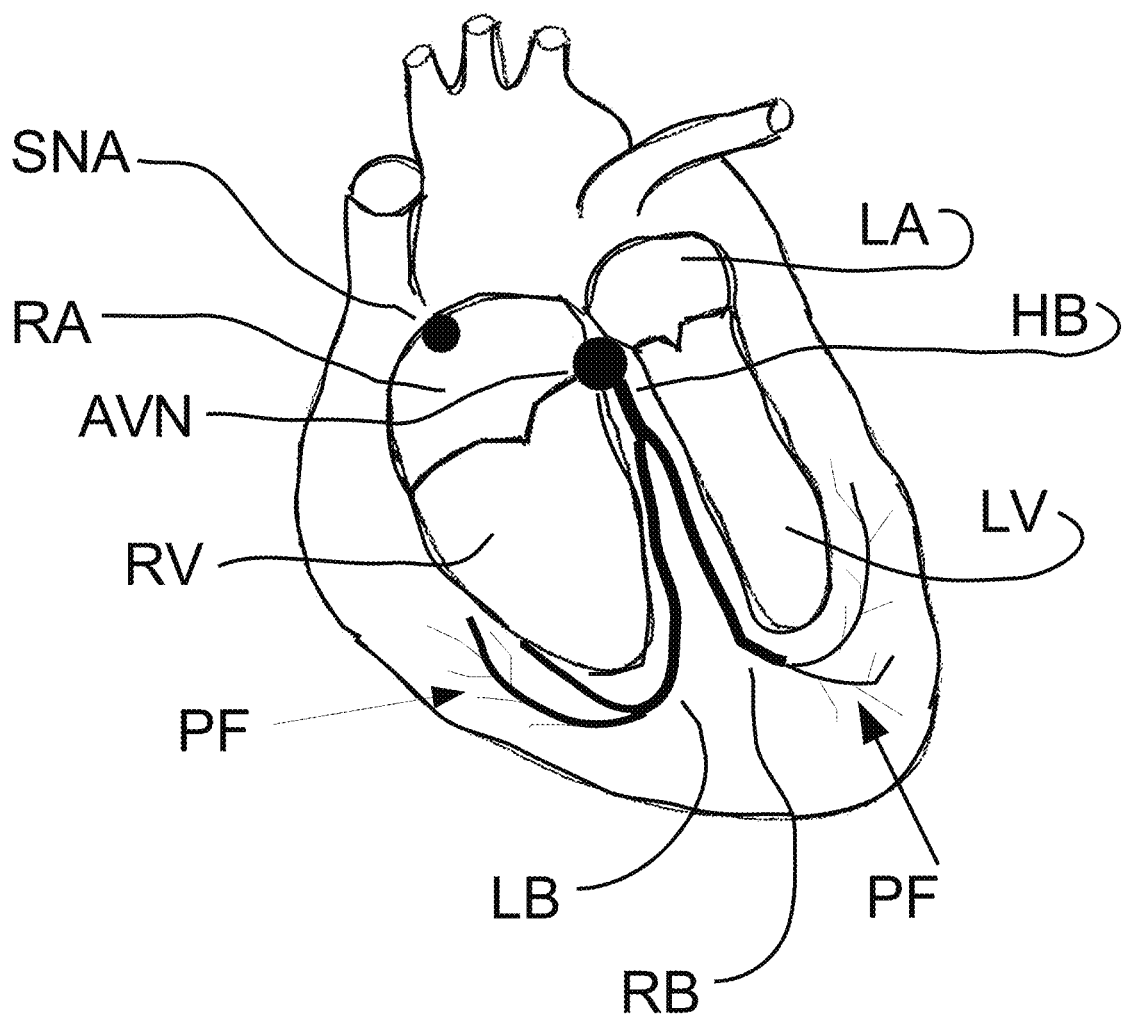
Figure 2:
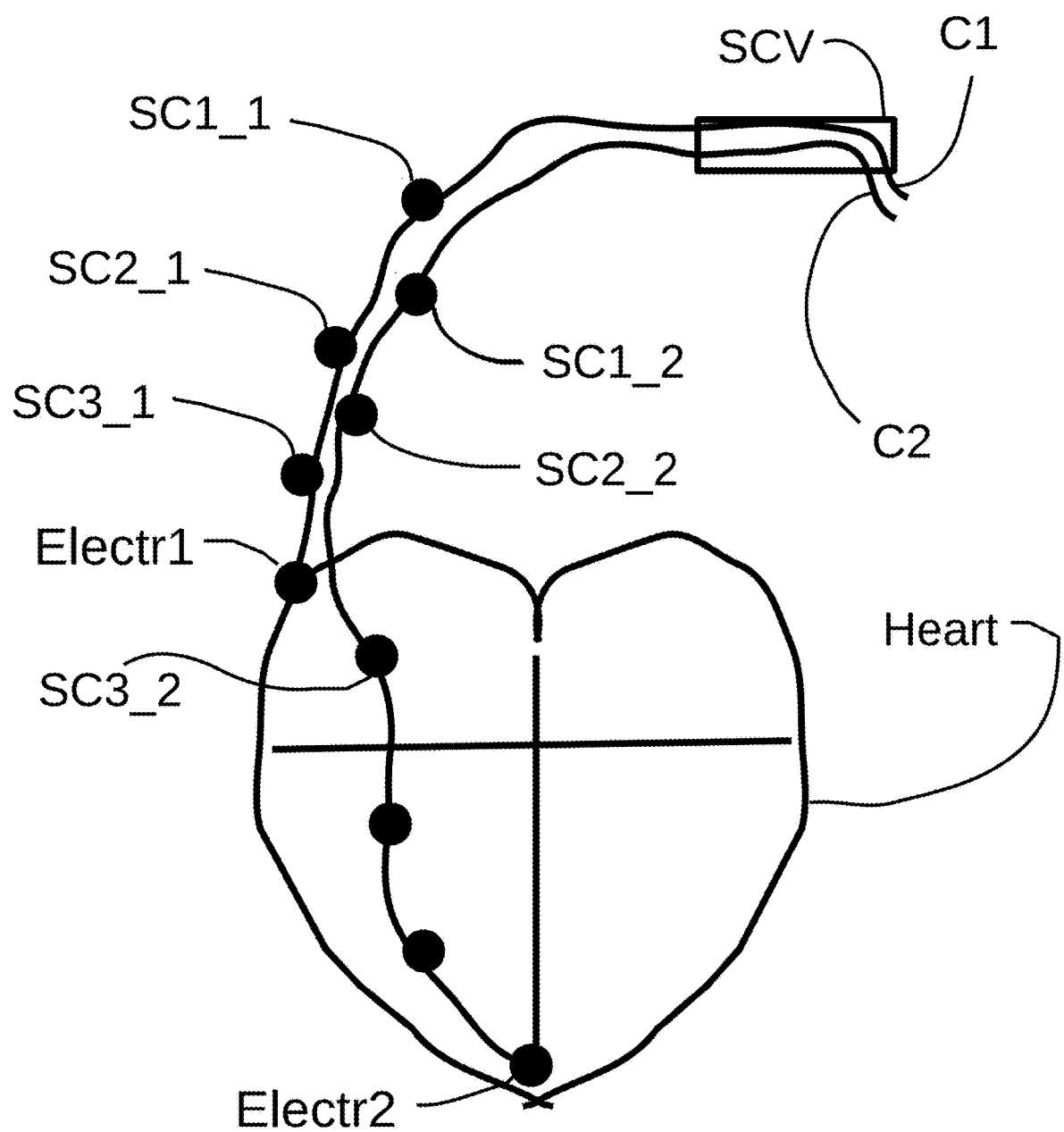

To understand the operation of our invention, the reader must keep in mind what causes the heart to contract, and therefore to pump the blood, and the sequential nature of this contraction as well. FIG. 1 displays a human heart with the main parts indicated in it. Left and right are designations from the point of view of the person in which the heart is, which is the opposite of the viewer, facing the person. The right and left sections are responsible for two independent closed cycle blood flow: the right side of the heart pumps blood to the lungs then back is the pulmonary circulation, while the left side of the heart pumps blood to the whole body.

The heart muscle contraction occurs as a consequence of and following the propagating electric pulse that moves in 3-D (three dimensions) through the heart muscle from an initiating point (the sino-atrial node), which is located at the top of the right atrium—the 3-D electric pulse propagation through the heart muscle is important for the operation of our invention, as it will be seen in the sequel. This propagating electric pulse is known by the medical people as a depolarization wave, and the medical people associate a depolarization event to a muscle contraction event. This sequential contraction, characteristic of all peristaltic pumps, is similar to the process of squeezing toothpaste out of the tube: it is a progressive squeezing sequence which progress from the back to the exit port, as opposed to a simultaneous contraction from all sides. Granted that there are people that extract the toothpaste squeezing the tube from the middle, but it is universally acknowledged to be inefficient to do so, even by the very people that do it; they make a huge mess and drive other family members crazy trying to fix it all the time. The heart squeezes as a properly used toothpaste tube, not as a collapsing air balloon that collapses upon itself from all directions at the same time. Yet, the heart is not as good as it should be at squeezing from back to exit, and out invention improves the heart, directing it to go into a properly sequential squeezing.

One of the reasons for the lack of appreciation of this sequential contraction is that it is not perfect, as if it occurred within a well-engineered pump. Moreover, the heart is more or less hanging inside the upper torso, suspended by the blood vessels and somewhat resting on the diaphragm, as opposed to a proper peristaltic pump, fixed in relation to the machine in which it works. As a consequence of this, the heart twists and moves on all directions as it pumps, a dance masking its sequential motion. This dance of the heart, this twisting on all directions, should have been already noted as a sign that the electric pulse propagation along the heart muscles is not uniform, and that therefore neither is the contraction propagation symmetric around the heart, downwards at the atrium and upwards at the ventricles. Lastly, each half squeezes in ½ second, too short a time for a human being to perceive in detail other than from a slow motion video.

This sequential contraction is valid for all four heart chambers: the right atrium, which has its entrance at the top and exit at the bottom, contains the initiating electrical cells at its top (the sino-atrial node), from which the electrical pulse propagates in its muscle walls from top to bottom, which is, accordingly, the sequential squeezing, as per FIGS. 8A, 8B, 8C, and 8D (the figure exaggerates and distorts the situation for display purposes and because the inventor is unskilled in drawing too). The ventricle, on the other hand, has both entrance and exit ports at its top, which poses a difficult problem to solve, needing as it does, to contract from bottom to top, to force the blood to exit at the top, while the electric pulse is coming from the top! This was solved by the intelligent designer with a mechanism to arrest the electric pulse at the bottom of the atrium (else the ventricle would contract from top to bottom, where there is no exit point for the blood!), and another specialized set of cells, the atrium-ventricular node, which, upon receiving the weak electric signal that is coming down from the sino-atrial node, re-start another electric pulse, but with a few milliseconds delay, which is in turn delivered for propagation through a set of specialized fast propagating cells lining the wall between the two ventricles: the His short bundle, followed by the right and left bundles, and finally the Purkinje fibers that spread the electrical pulse throughout the bottom and sides of both ventricles. This second electric pulse, delayed from the initial pulse from the sino-atrial node, is then injected at the bottom of the ventricles, from where it propagates upwards, causing an upwards sequential contraction (in the opposite direction as the initial atrium contraction!), as required by an exit point at its top. This process of upwards contraction of the ventricle, the lower chamber, is displayed in figure FIGS. 9A, 9B, 9C and 9D. It works, though any respectable engineer would have made a different design, with a ventricular exit at the bottom, not at the top, but at least one can take solace in that this is not the worse design error of the human body—one just has to look at the brain.

The left heart pumping in essentially the same, varying only in minor details, there is no need to repeat.

This said, the reader should keep in mind two important points here which is the detail on which the whole invention hinges, and which we urge the reader to pay attention and ponder on. First, that not only is the heart contraction caused by an electric pulse but also that this electrical pulse, because it relies on the propagation of heavy positive ions in a viscous medium, it propagates relatively slowly through its muscles and special fibers. The propagation of this electrical pulse is very slow as far as electric events happens, the whole process taking just below one second to complete (at a normal heart beating rate of 70 beats per minute). This means that the times involved are of the order of 10s and even 100s milliseconds. This slow propagation time is important for our invention to work, as it will become evident in the sequel. The much faster propagation of electric charges in wires and transistors (1 million times faster), allows that a human-engineered circuit can take over the natural process and improve on it—a very interesting project indeed!

In this main embodiment, the variation and improvement over our previous cited patents Lee275 and Lee969 is that at least one (and perhaps as many as all) the field shaping electrodes (called passive electrodes in these two older patents applications) is placed under the surface of the supporting structure, as 131 and 132 for the cordum. This has two major effects. The first consequence is that once the field shaping electrodes are located under the surface of the support, it follows that there is a larger surface area available for them, which, in turn, causes that these subsurface electrodes can fulfill better the Dirichlet's condition (see below) for a closed surface completely enclosing the desired volume where one intends to adjust the electric field. We remind the reader that the electric field created by these subsurface electrodes is configured to apply a force on the propagating electric charges in the space surrounding the electrodes or surrounding the body of the electric stimulating assist system, guiding the propagating electric charges on a target path and/or to keep the propagating electric charges inside a target volume. The target volume may be a part of the brain, as the sub-thalamic nucleus (for DBS), or a part of the heart, as the walls of the heart muscle. The problem of the heart is more complex than the problem of the brain, because the heart requires a charge propagation that causes an efficient peristaltic pumping of the heart, with a forward squeezing of the heart.

The second consequence is that once the field shaping electrodes are located under the surface of the support, there exists a larger available surface area to be occupied by the active electrodes, or electric current injecting electrodes, which in turn increases the options for the electric current injection in the tissue.

Another improvement on the system we are describing here is the possibility of an addressing system with associated memory, which is also capable of receiving data conveyed by electromagnetic waves, as radio waves, FM, and higher and lower frequencies, which carry the addresses and other information necessary for the selection of a plurality of one or more electrode of each type (active and field-shaping electrodes) to be active, and also the electric potential value (voltage level in American parlance). Such system and many variations of them are disclosed in many other of our patents, particularly U.S. Pat. Nos. 8,335,551, 8,509,872, 8,538,516, 8,565,868, 8,738,135, 9,037,242 but also other patents too.

The shape and size differences for the electrodes is not necessary for the main embodiment, which would also work with stimulating active electrodes (and non-conductive field shaping electrodes) of the same shape and/or size. The invention is the same for simpler electrode arrays which may be simpler and less expensive to produce, such a choice being a matter of production/cost compromise, still under the scope of the main embodiment. For example, it is possible to control the vector injected electric current (magnitude and direction) with circular electrodes (of either type, conductive or current injecting and insulated or field shaping electrodes) that are of different sizes and randomly distributed on the surface of the cordum. It is also possible to control the vector injected electric current with circular electrodes (of either type), that are of the same size and randomly distributed on the surface of the cordum, in this more restrictive case, same shape and size but randomly distributed on the supporting surface. Or it is also possible to control the injected electric current vector with circular electrodes that are of the same shape and size and orderly distributed on the surface of the cordum, this being the most symmetric electrode arrangement of all. The difference between these options is simply the degree of possible variations and fine control on the vector current, and the choice between each option is based on a cost/benefit analysis, all being still within the scope of our invention.

A moment of thought will show the reader that the good operation of the heart depends on the propagation of the electric current. This latter depends on the electrical characteristics of the diverse muscles (cells) which comprise the heart, including rapidly electric propagating cells (His fibers, etc), endocardio and miocardio cells, the electric characteristics of which suffer individual variations from person to person, due to their genetic make-up, to which other variations accumulate during the person's lifetime, due to his exercise and eating habits, etc, to which unlucky events as small localized infarctions add scar tissues to do possible broken hearts in the youth of the person, each described by a potentially lower conductivity and loss of contraction capability, all adding to a conceptually simple problem, yet of complex analytical solution. This, in turn, is the problem which our invention address: how to better adjust the 3-D electric current propagation through the heart in order to cause the best heart squeezing sequence possible for a particular individual, given his possibilities as determined by the physical conditions of his heart at the given time when the device is installed in the patient.

Another way to say the same thing is to notice that unlike a standard electrical network, on which the paths are discrete and fixed, the electrical path for the current that produces the muscle contraction is continuous over the whole 3-D structure of the heart, and some leak out of it too, being measured as EKG signals on the chest. Because the former, a standard electrical network is composed of discrete, enumerable paths, the information is given as the denumerable branches and nodes, while in the latter case (the heart) the information is a continuous current vector field.

Besides selecting which electrodes are turned on or off (connected or disconnected from the electrical power), the controlling microprocessor MP1 can also select one of a plurality of electric potentials (voltages) to be connected to the electrodes. Varying the electric potential at the field shaping electrodes, the device can adjust the electric field in its neighborhood, and therefore it can adjust the path of the electric current that is injected elsewhere by the active electrodes. Moreover, the improvement we disclose in this document discloses buried, or subsurface field shaping electrodes.

This offers an advantage over prior art because out invention can better direct the electric current to the particular desirable target volume and avoid entering into undesirable volumes. Also, varying the electric potential (voltage) at the active electrodes, the device can adjust the magnitude of the current that is injected into the heart.

The Electric Field Lines.

Figure 10:
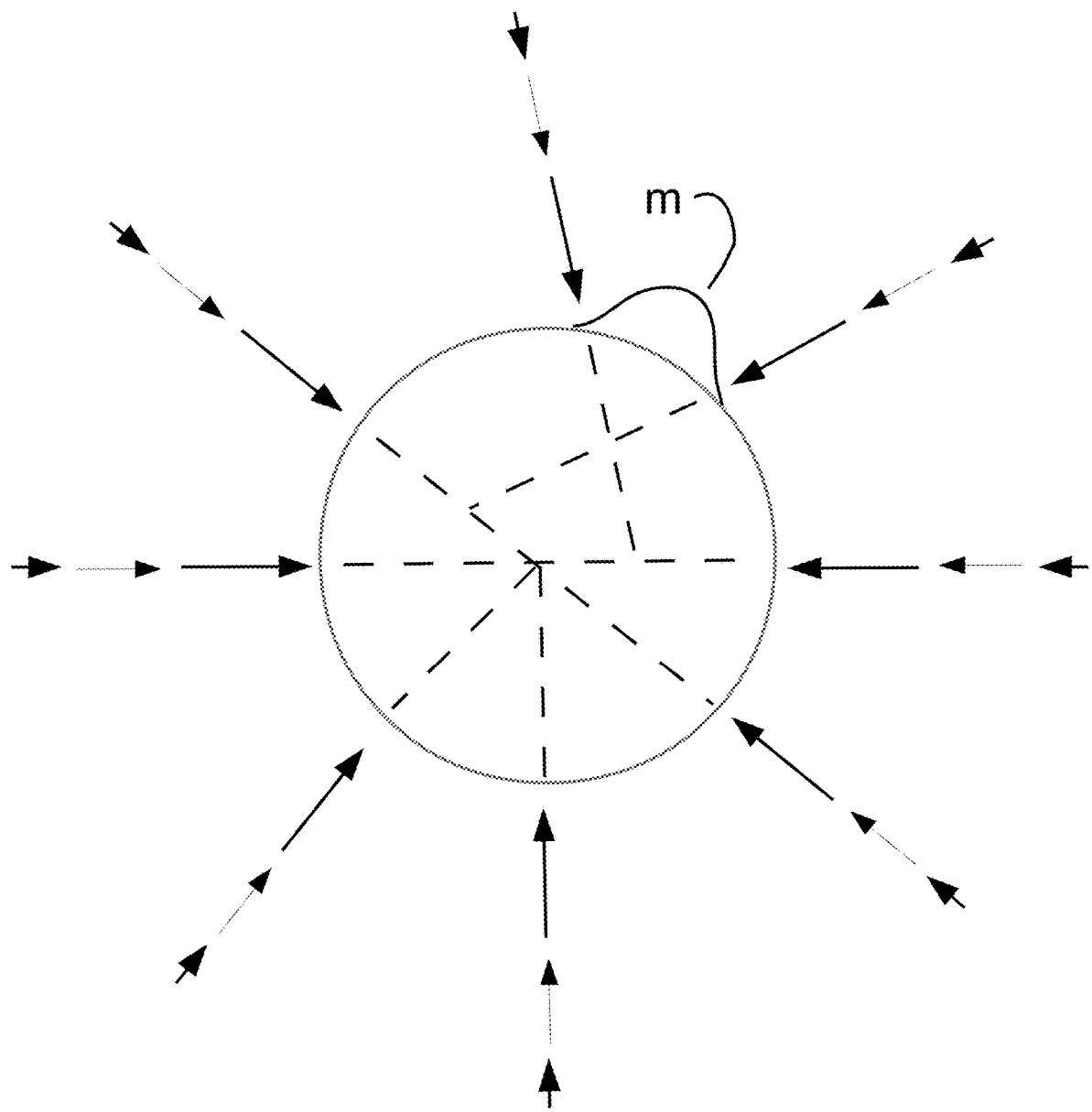

The solution to this problem is found in the theoretical analysis of electric current propagation within an electric field. As a side remark, this is similar to the motion of an object by gravity within the gravitational field of the planet, which is vertical towards the center of the planet assuming a perfectly spherically symmetrical Earth. All objects, unless prevented from falling by some means, do fall down in the direction of the center of the Earth, on a straight vertical line. The earth gravitational field is set of lines radially pointing to its center, as most of the fields in FIG. 10. FIG. 10 also display two gravitational field lines next to an exaggerated large mountain, which, due to its large mass tilts the gravitational field lines sideways towards the mountain. An actual large mountain does, surprisingly enough, minutely deflects the gravitational field from its "normal" direction towards the center of the earth, and in amounts that are detectable with modern equipment (see an exaggerated off-radial displacement near the mountain at FIG. 10). This, of course, happens because the mountain attracts sideways. Another example is an automobile while driven by a person at the driver's seat. The driver is capable of pressing on the gas pedal, which detonates a sequence of events that culminate on a faster speed of the car, and turning the steering wheel the driver detonates a different sequence of events that culminate on the change of direction that the car moves. Both of these, the speed and the direction are controlled by the electric field lines acting on a volume where electric ions (Ca, K, etc., in a heart) can move in several directions and at different speeds as they are acted by the electric field lines, as shown below.

Given that $$F(\text{vector}) = q \times E(\text{vector}),$$

Figure 11A:
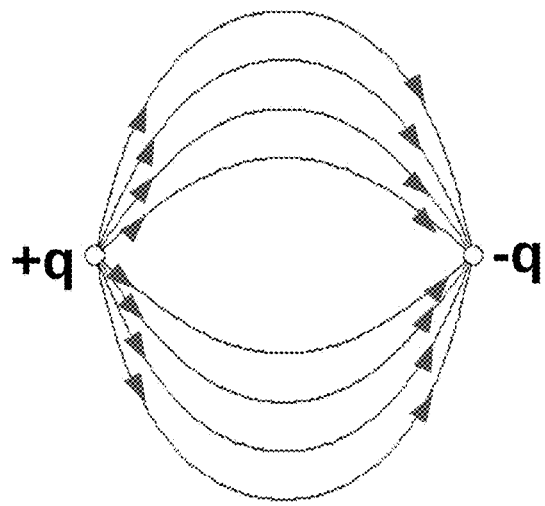
FIG. 11A show a calculated field line around three possible electric charges distributions.
Figure 11B:
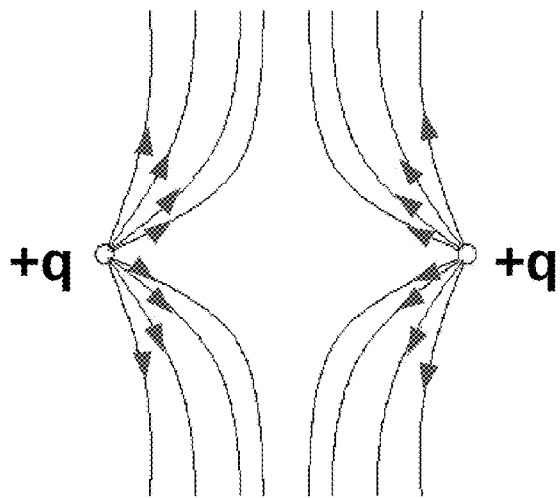
FIG. 11B show a calculated field line around three possible electric charges distributions.
Figure 11C:
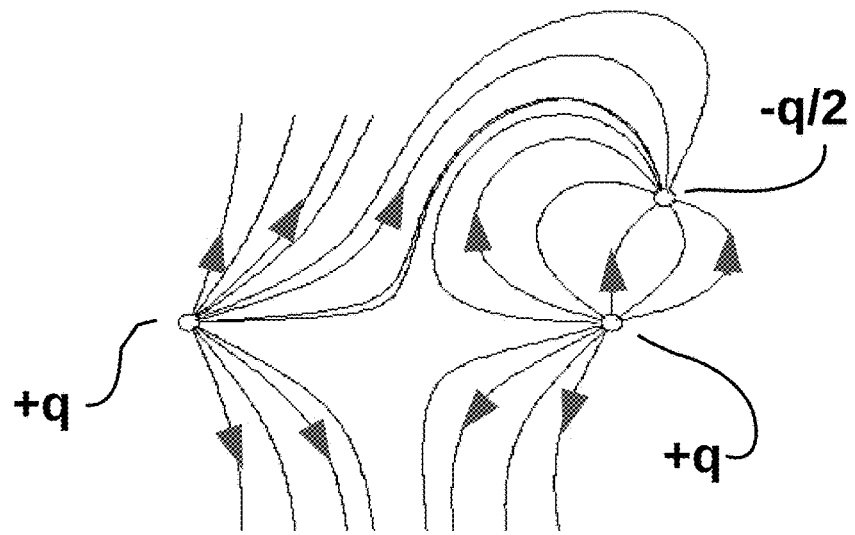
FIG. 11C show a calculated field line around three possible electric charges distributions.
Figure 11D:
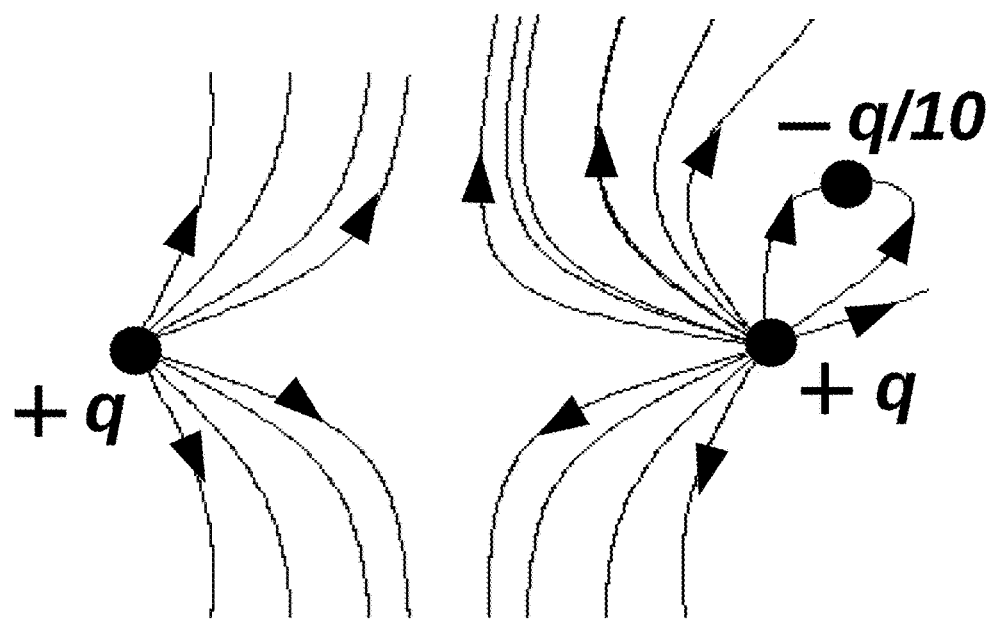
FIG. 11D show a calculated field line around three possible electric charges distributions.
Figure 11E:
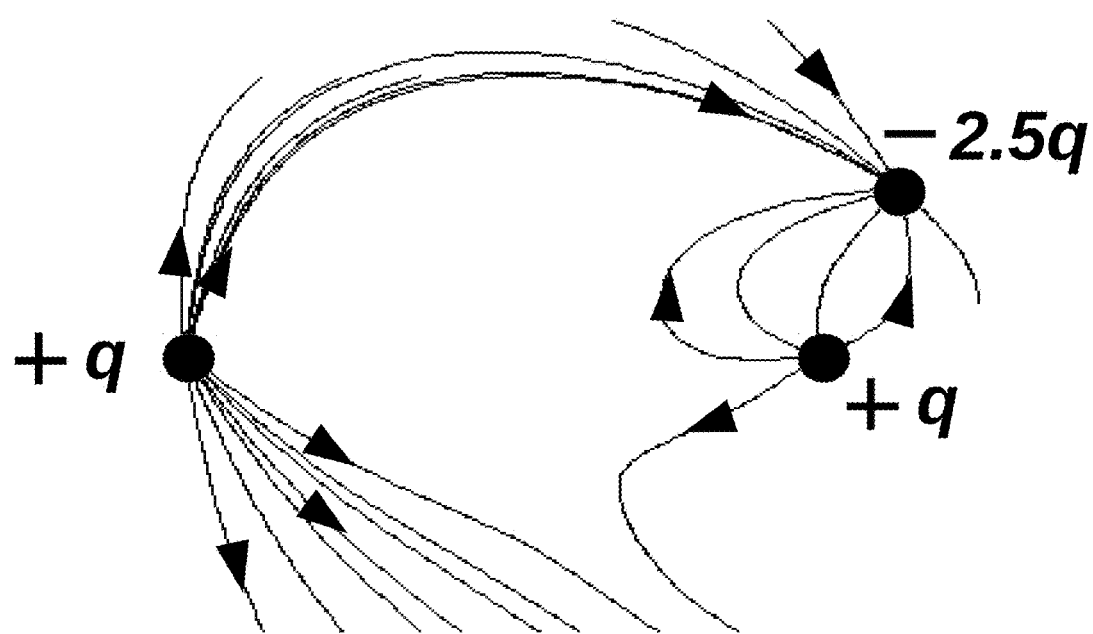
FIG. 11E show a calculated field line around three possible electric charges distributions.

It follows that the force, and consequently the acceleration and then the motion of an electrically charged particle starting from rest are determined by the electric field lines. The electric field can take more complex configurations than the gravitational field, because there are two types of electric charges (usually called positive and negative), while the gravitational field is due to only one type of gravitational charge (called mass, they all attract each other). FIGS. 11 (A, B, C, D and E) displays five types of simple electric field configurations: Figures FIG. 11A and FIG. 11B display two cases of field lines that are simpler to calculate, of two electric charges, in fact the configuration normally seen in introductory physics books, books used in middle school in most of the world, and used at university courses in USA. The field lines are the lines along which forces act on electric charge moving in the volume. In other words, the field lines control the flow path of the injected current. From this it follows that to shape the electric field lines is the same as to lay down the "roads" where the current will travel whenever charges are set free in the region. This notion of shaping the field lines to determine the current path is seldom used only because in most electric circuits the current (charge) is forced to follow the wires, the coils, the transistors, etc., with no place for an externally imposed electric field to have any effect. FIG. 11C shows a more complicated case with three charges. The reader is invited to observe the large change of the configuration of the field lines caused by the addition of this third charge, in particular the disappearance of the symmetry that is obvious in figures FIGS. 11A and B. FIGS. 11D and E display the effect of varying the value of the third charge. Again the reader is invited to ponder on the consequences of varying the values of the charges. Notice that both FIG. 11D and FIG. 11E are asymmetric, yet the shape of the field lines is vastly different between them!

The electric field lines are distinctively unequal, very different shapes. Not displayed is also their strengths, which is also distinct, left out to simplify the figure. FIG. 11 illustrates the point of our invention: a method and a means to conform the electric field lines to the desired 3-dimensional shape required for a most desirable heart squeezing sequence. In fact, using the cordum of our invention, it is possible to even create a 3-dimensional electric field which causes a better heart squeezing sequence than the sequence that happens in a normal, healthy heart, because a normal, typical, healthy heart does not actually follow the best possible sequence due to its design having been unintelligent.

Setting each small electrode at the sub-surface of the cordum at a different electric potential (which causes a different electric charge Q on each electrode), a different electric field is set in its neighborhood. The cardiologist, or any other medical personnel, using a computer program to display the electric field created by any particular combination of voltages, will adjust the voltages at different electrodes and see, on the computer screen, the 3-dimensional conformation of the electric field created by them. This is one problem of the class known as "inverse problems", a technical name given in mathematics for problems in which a particular cause is sought (a particular distribution of electric potentials (voltages) on the surface of the cordum) which will cause a particular 3-dimensional electric field configuration over the heart muscles. Mathematicians have goose bumps when they are presented with an inverse problem, because they know that most inverse problems have no solution (no closed form solution, to be precise), which is the case of this one. Its solution is found by trial and error, adjusting a new electric potential at the field shaping electrodes and noticing if the new electric field got closer to the desired one or farther away from it. From this, readjust the electric potentials and observe the result again, and again, etc. Though this may seem a tedious solution, it is easier than working from scratch, because the hearts are approximately the same, and the pacemakers are implanted in approximately the same places, which means that the general type of solution needs to be found once and for all—then only smaller adjustments are necessary. In any case, if so desired the cardiologist can set all the active surface to be at the same electric potential (voltage), in which case the "improved" electric stimulator (pacemaker) would be working in the same way as prior art pacemakers.

In practice, the inventors believe that even without individual adjustments, and only using the best average selection of surface distribution of electric potentials (voltages), there would be some improvement over prior art.

Current art of heart pacemakers uses two and even three individual electrodes, for example, one electrode near the sino-atrial node (at the top of the right atrium), and one near the bottom of each ventricle (right and left). Using these multielectrode stimulators much enhance the performance of our invention, because they increase the number of available points over which there is control for adjusting the electric potential (voltage V, as the Americans say) (or charge Q, which is the same thing), and also at much larger distances between them. More control is possible with the modern two- and three-stimulators than with the one single electrode at the top of the atrium.

Besides the directional electric current flow, which is started again at every heart beat at the sinoatrial node, the local reactance plays a role, as it determines a 3-dimensional continuous network which determines the time delay and magnitude of the local electric pulse, which in turn determines the local timing and strength of the local squeezing. Incorrect time delays of the electric pulse are costly for the pumping efficiency, because since they are the very cause of the muscle contraction, that is, of the pumping, and therefore time delays on the ion propagation through the heart muscle are reflected in time delays in the contraction sequence. Localized higher or lower resistivity are costly too, because they change the electric current density, which in turn decrease or increase the strength of the muscle contraction, that is, of the pumping pressure, either way decreasing the total pumping volume. Our invention, as it adjusts the magnitude and the direction of the electric field throughout the heart muscle, corrects for these errors that accumulate throughout the life of the person, as the heart ages and changes. For example, in locations which, due to the changes that occurred throughout the life or due to genetics, the resistivity is larger (which decreases the electric current and its speed), they can be countered with a locally larger magnitude electric field.

Taken together, controlling the direction and the magnitude of the current, our invention is capable of controlling the position and the magnitude of the squeezing sequence.

Introduction to the Mathematical Treatment of the Problem of the Best Electric Current Distribution Over the Heart Muscle.

It is a well known result in electromagnetic theory that any arbitrary vector field inside an imaginary closed surface obeying the Maxwell's laws the govern the electric and magnetic fields can be created adjusting the electric charge distribution at the surface that encloses the closed volume (see Reitz, Milford and Christy (1980), Jackson, (1975) or most any other introductory text in electromagnetic theory). This physical statement is related to the Dirichlet's principle DIRICHLET (n/d). But the reader is reminded that the Dirichlet's principle applies to electromagnetic waves described by the known $2^{nd}$ order differential equation, which is not the case here, because here the electric field is static, not dynamic. In our case the stimulating device does NOT have total control, because it would be impossible to set electric potentials (voltages) at unconstrained values (the electric energy source (or electric energy storage unit)/battery is rather limited on its maximum output), nor do we have access and control over some surface that completely encloses the heart (or the brain, etc.), which means that not all desired vector fields are possible. Yet, adjusting the available electric potentials (voltages) over the available surface on the device in the vicinity of the desired volume it is possible to have a certain degree of control of the current vector field over the heart volume, and consequently to have more control on the path and speed of the injected electric electric charges and better results for the patient. This is even more correct when the cordum stimulator is, as is becoming more common nowadays, a three independent stimulators, one at the top right atrium, one at the bottom of each ventricle. Our invention does not create a total control on the field lines, our invention cannot create all arbitrary field shapes, but our invention can shape the field to a better conformation than old art which offered no control of it. In fact, to the best of the knowledge of the inventors, nobody before have ever tried to control the electric field shape on the heart muscle to control the current through it. It is to be noted that the invention disclosed in this document allows for a larger Dirichlet surface surrounding the volume of interest then the devices described in the two previous invention disclosure of ours: Lee275 and Lee969.

Dirichlet's problem is discussed in books dealing with electromagnetism because it is much related to the problems of interest in the field, yet it was initially developed out of its mathematical interest, and it is also discussed in many books in differential equations.

This mathematical theory indicates that our invention works better with either a larger area supporting electrodes (which approaches a totally containing surface) and also with just a few small electrodes spread apart, as in the two- and three-electrodes of current heart pacemaking, anchored as they are, at the top of the right atrium and bottom of each ventricle.

Therefore our invention is the use of a controlled charge distribution (or voltage, which is the same, because one determines the other) over as large an area as feasible, with the objective of adjusting the electric field lines over the heart muscle so that the injected current causes a downwards moving current from the top of the atrium to the boundary between the atrium and the ventricle, then either another current through the His bundle, right and left bundles and Purkinje fibers, or else simply another starting electric current originating on another implant at the bottom of the ventricle, possible if the cardiologist decides to use a two-electrodes pacemaking system. Moreover, the surface electrodes can be of either type 1 (active) or type 2 (field shaping). The first type of electrode can be either starting or finishing points for electric current paths, while the second type of electrodes is able to bend the field lines but not able to inject charges, because it is electrically insulated (though it can act via capacitive effect, as well known to the persons versed in the field of electrical engineering). Finally, given that the times involved are very long for electronics, a typical heart period being almost a full second and its P, Q, R, S and T waves lasting from a few to 100s milliseconds, while microsecond is easy in electronics, it is perfectly feasible to activate electrodes or either type (active or field-shaping types) then turn them off sometime before the slowly moving electric current arrives at the electrode, therefore forestalling the establishing of a terminal point for a current. This can be dynamically adjusted to keep the current moving along a desired path, while never absorbing it. This selective adjusting of the ending points of an electric field line is effective in creating strong field lines with the use of electric charges near the initiation point of the current, which in turn is made to disappear as the current nears intermediate positioned electric charges, which may be substituted by other charges further along the desired path, all working as a carrot moving ahead of a running rabbit. Of course that the reverse action can be also created, of a same sign charge being introduced behind the moving current, in which case this same charge could be seen as akin to a whip at the back of the moving current, a horse-type incentive added to a rabbit-type one.

Two and three electrodes heart pacemakers are becoming common nowadays, and more electrodes may be used if a good reason for them is discovered, as our invention does. Even three anchored heart cordums in three different places already open new possibilities for shaping the electric field; more than three offer even more possibilities.

DESCRIPTION AND OPERATION OF ALTERNATIVE EMBODIMENTS

FIGS. 20, 21, 22, 23, 24, 25, 26, 27 and 28 are directly related to this continuation-in-part patent application, while the first 19 figures are either less applicable to this case here, or not applicable at all, being included only for being part of the grand-mother and mother patents. Let us start analyzing this invention from the general point-of-view of the grand-mother application, emphasizing the differences and the new, then later, at the end, discuss the specific points that are distinct and only part of this patent application discussed here. We will use the particular case of breast cancer biopsy as an exemplary use of our invention.

As a general comment, this patent only differs from the parent applications on being applied to a particular group of devices, which are the devices used for collecting cell samples from animal tissues suspected of malignancy, which cells will later be used by a pathologist for a final decision on the type of growth, on it being malign or benign. The reader is here warned, which she/he already knows, that the final decision about the nature of the growth depends on a pathologist's examination, which, in turn, means that tissue sample collection is fundamental for any final decision regarding what to do, which means that the sample extractor (Ex) is an important device, which is part of every cancer treatment, several hundred thousands of cases per year only in the United States.

The parent applications deal with electrical stimulators for several objectives, which are different on each case, and, in general, for different objectives than the current application. For example, the electrodes used for heart, are designed to cause a better heart pumping fraction, or, in laymen's language, an energetically more efficient pumping cycle, while for DBS (Deep Brain Stimulation), the electrodes are designed to forestall the tremors of Parkinson's disease, etc. The first generation upwards, or the mother application, the patent just above this one, patent application Ser. No. 16/721,823, application date 2019 Dec. 19 now allowed, describes protruding electrodes, which are electrodes (140_t1, 140-t2 and 140_t3) attached to supporting structures that protrude out from the main supporting structure, with the objective of positioning the electrodes at a distance from the active electrodes (140_t1), locating them on the best places for having a desirable effect on the motion of the electric charges injected by the active electrodes 140_t1. Yet, a moment of reflection would bring to the attention of the reader that the protruding electrodes are what is needed to complement the necessary pain control for the medical procedure of extracting tissue samples from the inner part of the body for positive determination of malignancy, prior to cancer surgery. This is the last step before surgery is performed, several hundred thousand cases per year in the United States alone—a very important figure. This application of the protruding electrodes (from the mother application, Ser. No. 16/721,823) is the subject of this patent application.

Figure 26:
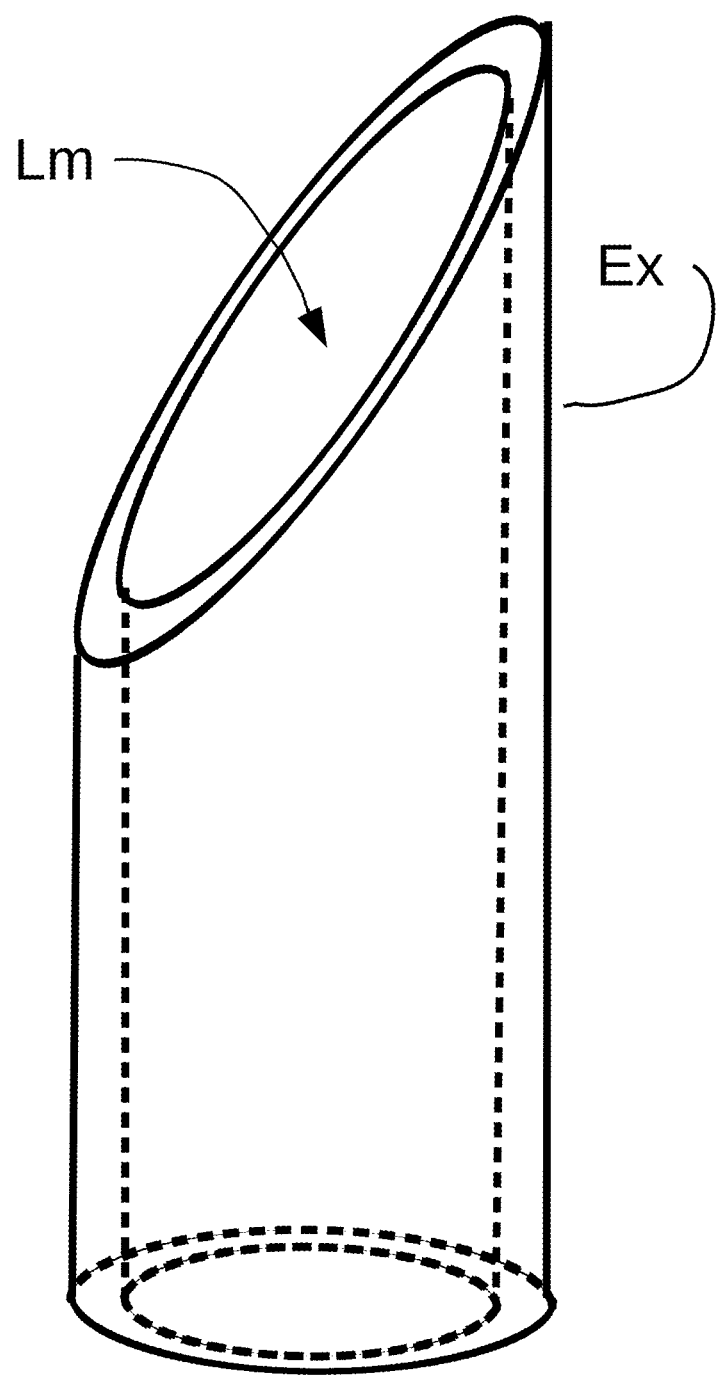
FIG. 26 shows one common, but not only, type of extractor Ex, the type that resembles a hypodermic needle, only much larger diameter, with its lumen indicated.

FIG. 26 shows one type of the extracting devices (Ex) used to extract tissue samples from the inside of the body. In simple terms it is a big hypodermic needle, typically 2 mm in diameter, but that may occasionally be 3 mm diameter or even rarely more; it is a really big needle, believe me!—very scary. Other types of tissue extractors Ex are in use, which we do not describe here for being outside of the scope of this invention. The type shown at FIG. 26 is only an example, other types existing, with variations, some of them for the better, some for the worse, some neutral, some just to get around existing patents, therefore existing just as a consequence of capitalism, nothing more, no real advantage, no real superiority over the previous models.

As the reader can see at FIG. 26, the extractor Ex is a device that can be inserted inside a muscle or inside an organ of a poor patient, with the objective of extracting sample cells from it, for later analysis by a pathologist. The extracted cells are sucked into the lumen of the needle. The inventors have recently taken the COVID vaccines, as probably the readers die as well. The COVID vaccine is applied with a needle that is 200 micrometers in diameter (on average, depending on the mood of the nurse that works on you), a needle 10 times as smaller than the extractor Ex used for tissue sample extraction! The inventors got scared at the thought of the needle, and even more scared at the sight of the needle, and we believe so did the readers; now imagine a 2 mm needle (a common size) or even a 3 mm needle, a rare but not impossible size, or even larger needles, almost never used for sample extraction! These extractors Ex are no joke, believe me! Of course that the unfortunate patient receives a local anesthetics—injected with a 200 micrometers needle . . . :), which makes the subsequent process a little easier.

Figure 20:
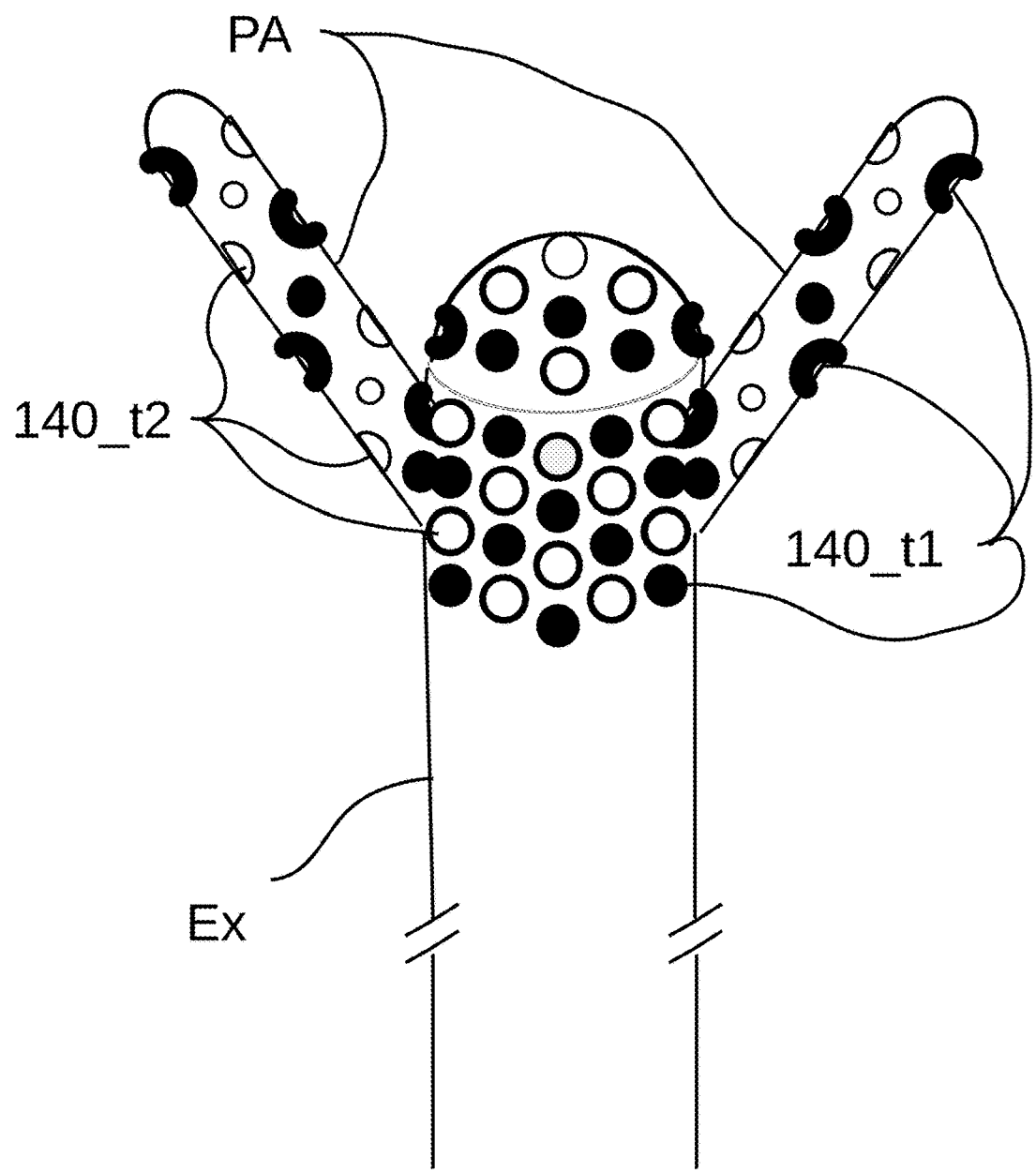
FIG. 20 shows a supporting structure for tissue extraction with the protruding arms or extensions of our invention.
Figure 21:
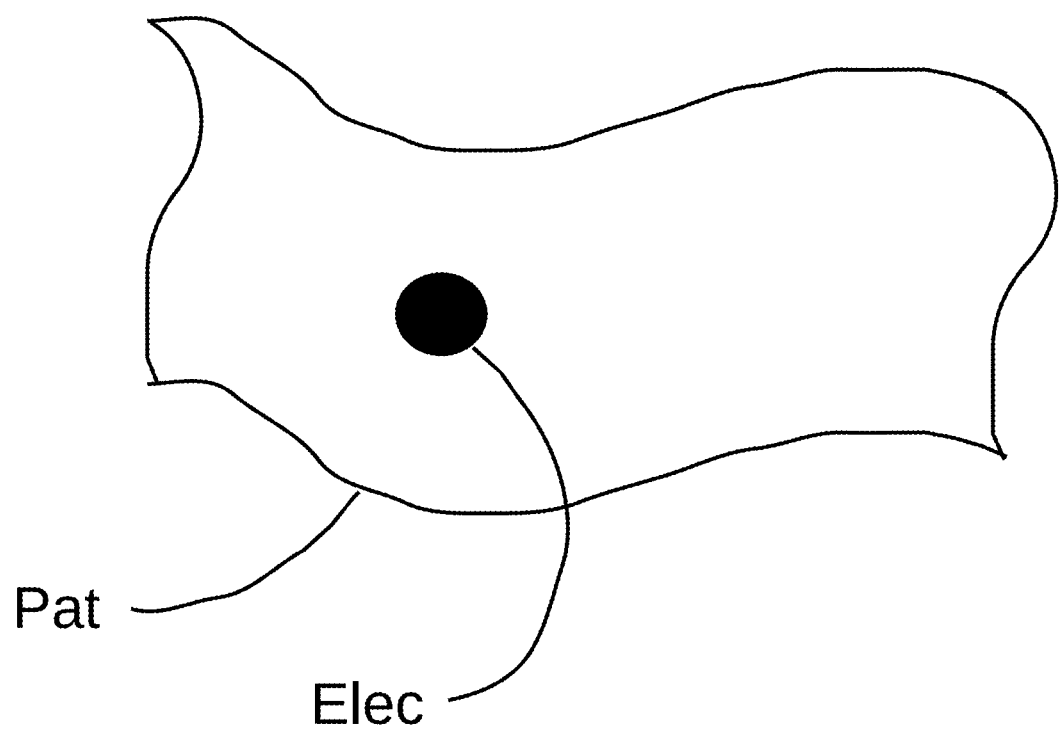
FIG. 21 shows an example of a second supporting structure separated from the first supporting structure with one single electrode.
Figure 22:
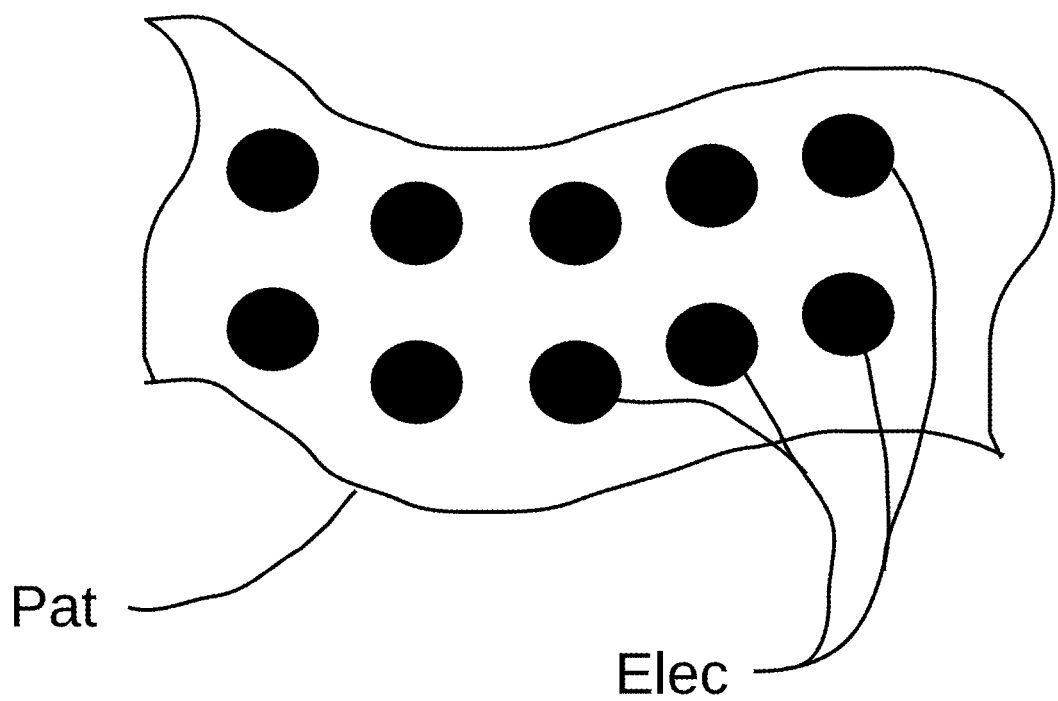
FIG. 22 shows an example of a second supporting structure separated from the first supporting structure with several electrodes.
Figure 23:
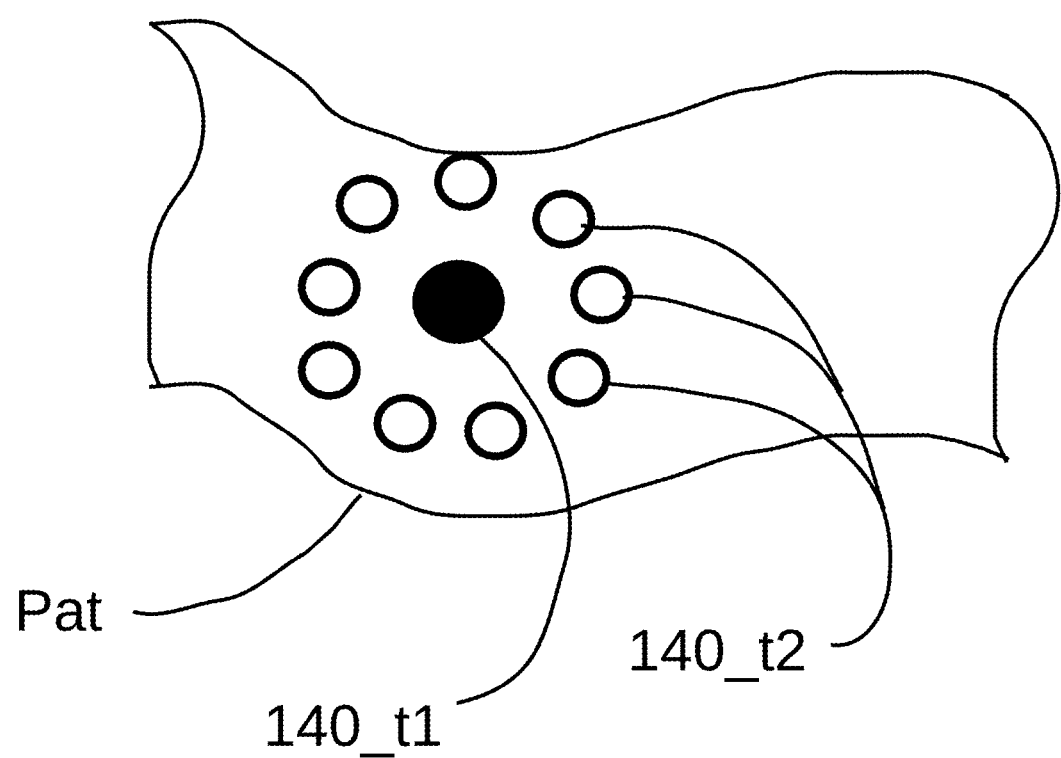
FIG. 23 shows an example of a second supporting structure separated from the first supporting structure with electrodes of type-1 and type-2.
Figure 24:
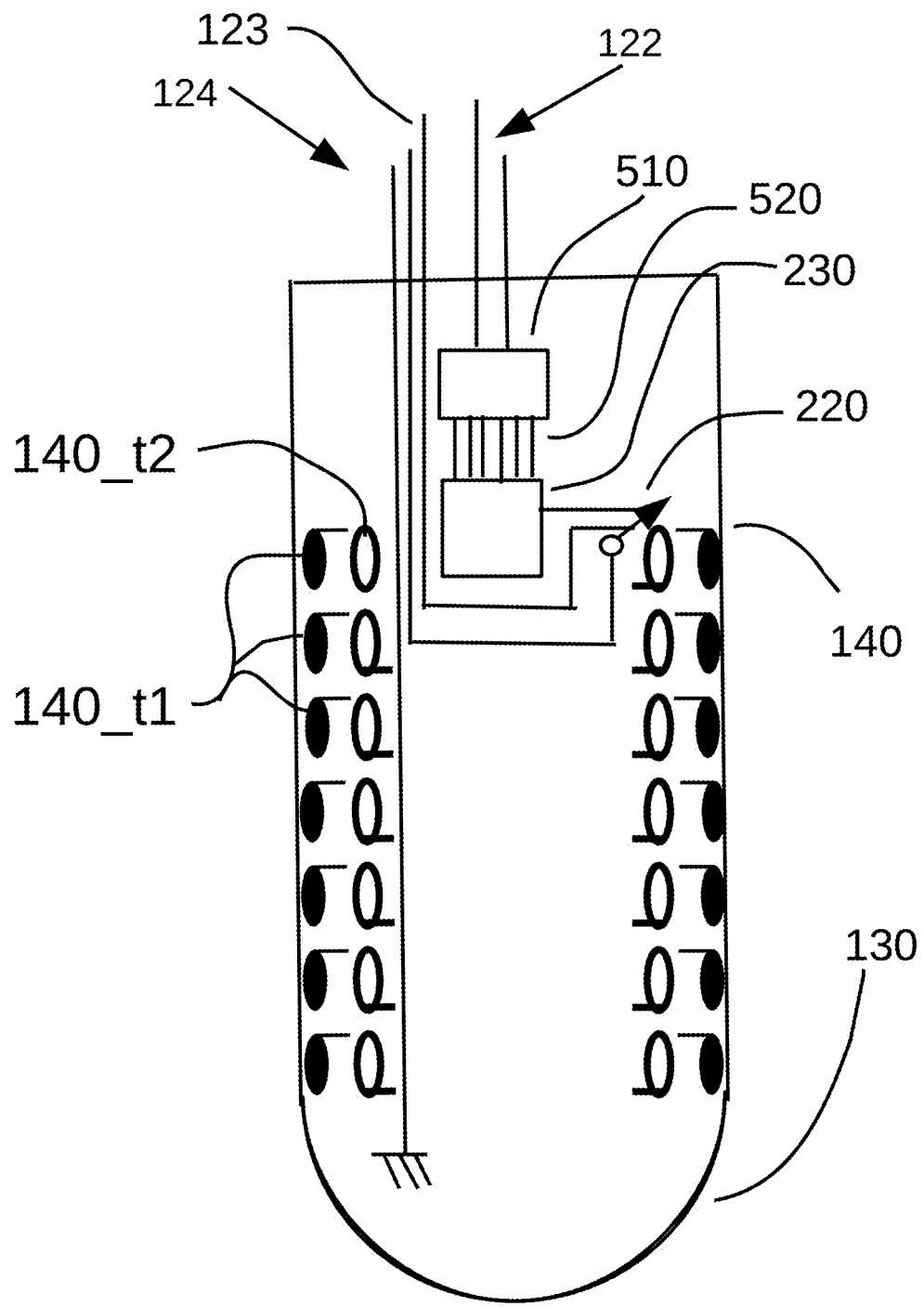
FIG. 24 shows an example of the extractor of our invention with electrodes of both types 1 and 2.
Figure 25:
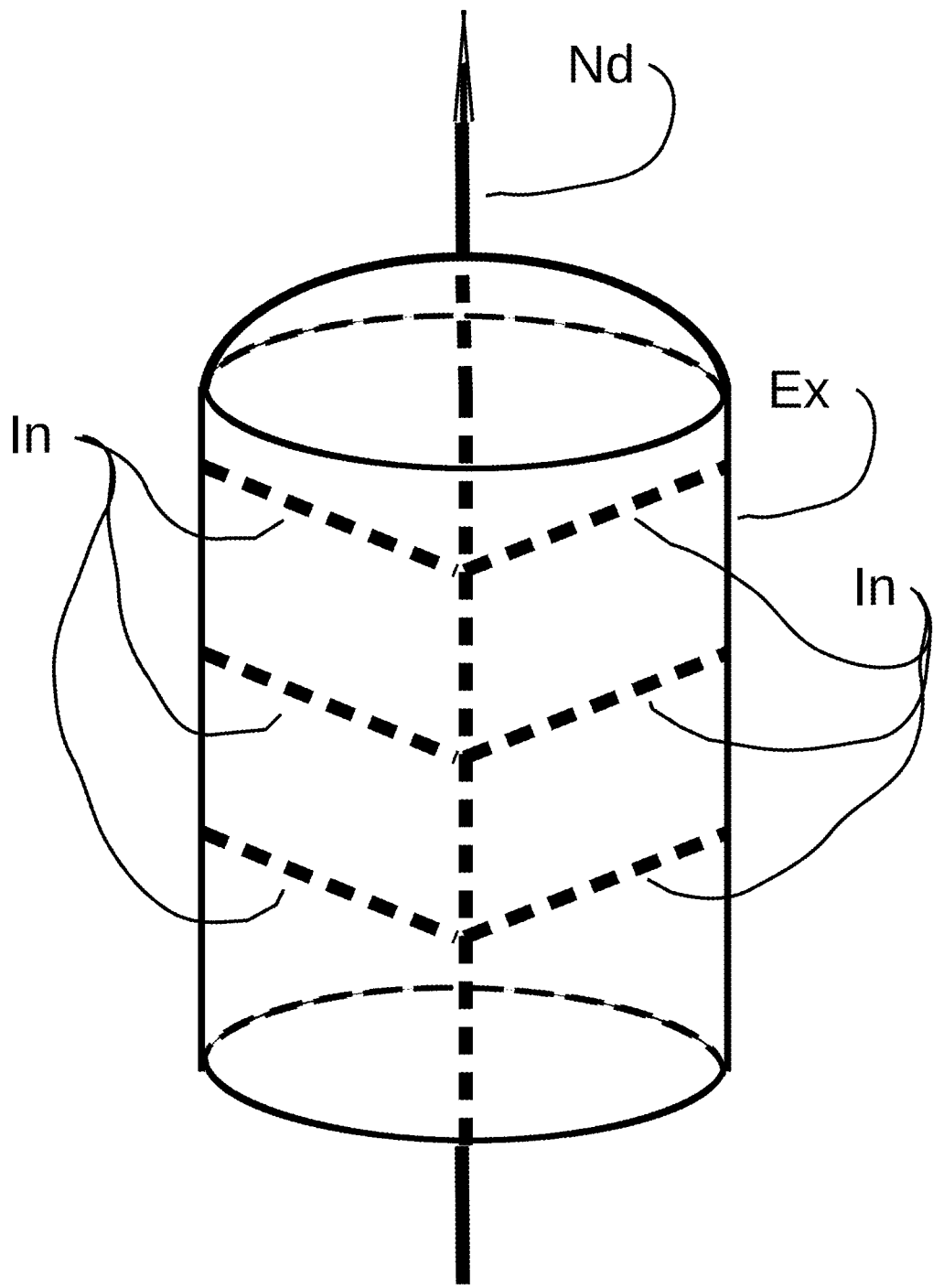
FIG. 25 shows an extractor Ex of our invention with a general-type distal end (hemispherical, that can be any of the used styles) with a needle Nd at its distal extremity and several injectors In leading to the sides of the extractor Ex
Figure 27:
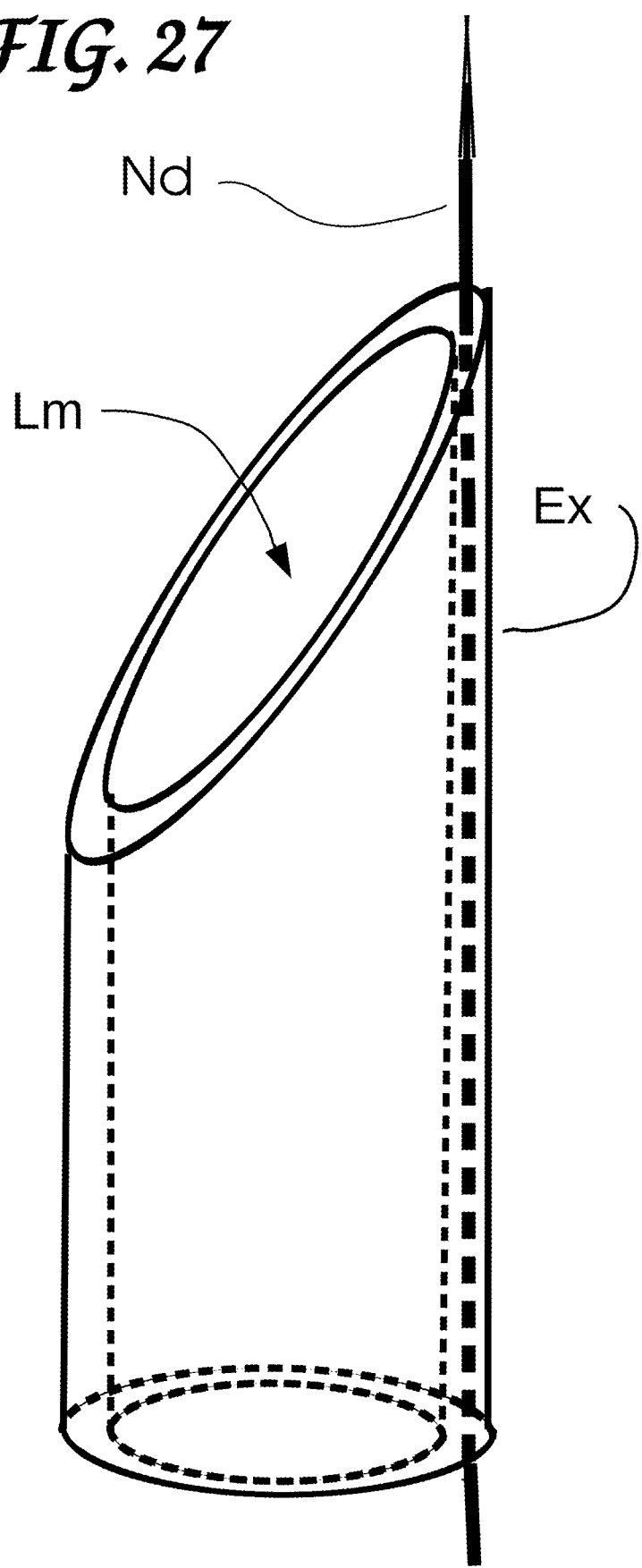
FIG. 27 shows the same type of extractor Ex shown at FIG. 26, with a needle Nd used for injection of more anesthetics if it is needed after the insertion of the extractor Ex.
Figure 28:
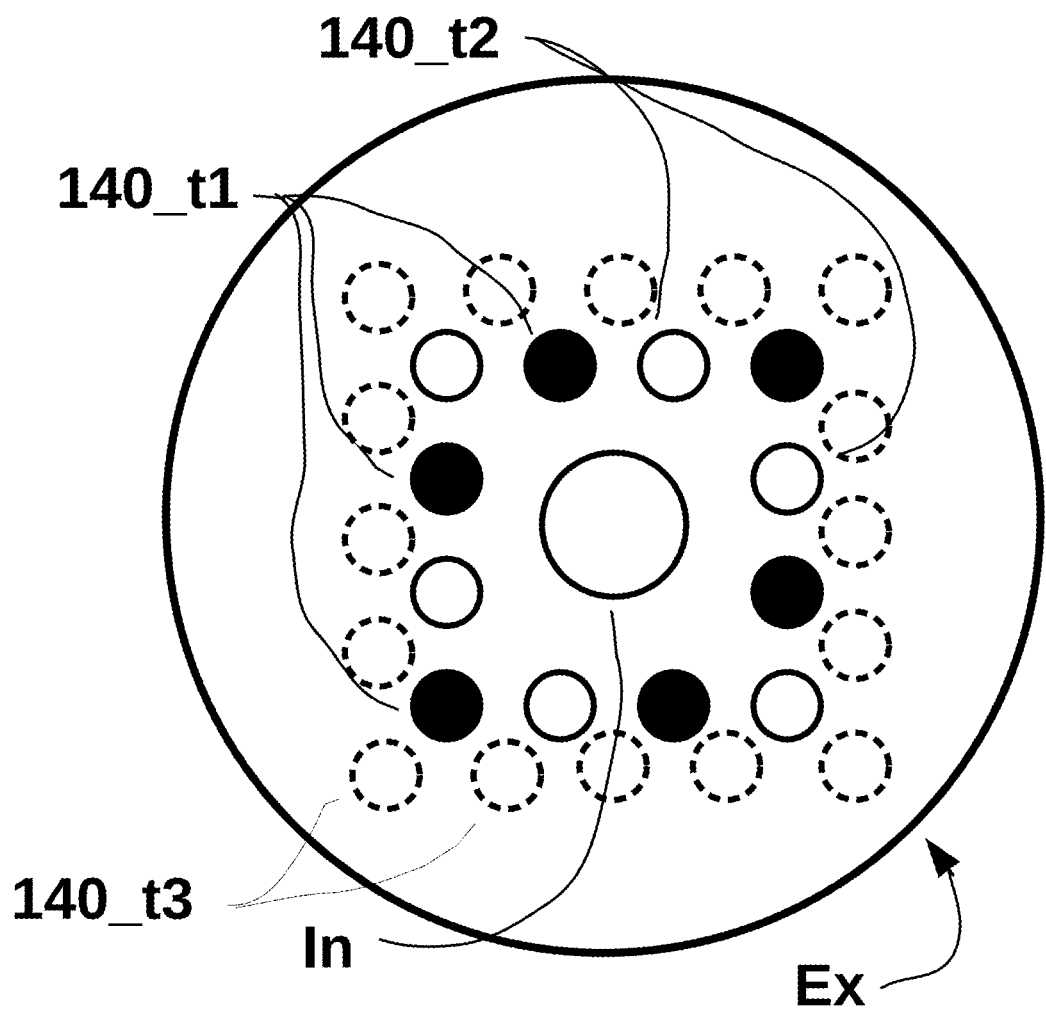
FIG. 28 shows the extremity of an injector In surrounded by several electrodes of all the three types, type-1, type-2 and type-3.

So we finally arrive (uff, mamma mia) at the invention of this patent application: the addition of a protruding needle Nd, also called here as second supporting structure, to the extractor Ex, also called here as first supporting structure. Both the needle Nd and the extractor Ex are capable of having electrodes 140_t1, 140_t2 and 140_t3, to act as a TENS device, adding a second layer of pain protection to the unfortunate guy that is being "extracted" by the "big needle" or extractor Ex. Our invention is shown at FIG. 27, which shows a needle Nd, capable of acting as a typical, old-style hypodermic needle, to add a second anesthetics into the patient, should it be necessary, and a bunch of electrodes at the surface of both the extractor Ex and the needle Nd (not shown in FIG. 27). FIG. 25 depicts a general extractor Ex, with a hemispherical distal extremity, which is shown in FIG. 25 as a hemisphere, only to be in place for one of the many existing extremities of the extractor Ex that are in current use, not all of which are as seen in FIGS. 26 and 27. FIG. 28 shows the end of an injector In, with several electrodes of the three types, 140_t1, 140_t2, and 140_t3, (type-1, type-2 and type-3, respectively). These electrodes are capable of injecting electric charges (140_t1) and of directing these charges, and other charges already in the body, on to the best path, which, in this case, is towards some nerve that is transmitting pain information to the brain, which nerve is then fooled into either not sending the "correct" pain information. Electrodes 140_t1, 140_t2, and 140_t3, (type-1, type-2 and type-3, respectively) are capable of working as TENS devices, decreasing the pain sensation on the patient. FIG. 24 shows the supporting structure 130 of the previous generation patent, now called extractor Ex to highlight the new use, with some electrodes of type 140_t1 and 140_t2, together with some of the electronics to connect them to the electric battery and to the electronic controlling device (not shown). The electronics is not shown in detail because it is well known by the electronics engineer (the persons with skill in the art, as the damn lawyers say it) Our invention also proposes a second supporting structure that is separated from the extractor Ex (first supporting structure). These separated second supporting structures have the function of positioning electrodes 140 of the three types, at locations at some distance from the extractor Ex, both to inject electric charges away from the point of injury, and to act as force generators, to apply forces F on the moving electric charges injected by 140_t1, guiding them to any desired nerve (not shown). These second supporting structures that are separated from the first supporting structure Ex may be, for example, located at the skin of the patient, similarly to a standard, old-time TENS device. One exemplary use of our invention is for breast cancer sample extraction, in which case the second supporting structure have the shape of a truncated cone which is positioned on the breast of the woman undergoing biopsy. But this is just an exemplary case, other possibilities existing, our invention not being limited to the case of breast biopsies. FIGS. 21, 22 and 23 depict three cases of electrodes 140 on a malleable sheet that is to conform to the shape of the skin of the patient, with one single electrode (FIG. 21), with several electrodes (FIG. 22) and with two different types of electrodes (FIG. 23). FIG. 20 depicts a first supporting structure Ex with some second supporting structures (marked as PA in this figure) with several electrodes of type-1 and type-2 on their surfaces. This is one of the examples used on the mother patent Ser. No. 16/721,823 (currently allowed), but here adapted to this more restricted application of cell sample extractor Ex (or first supporting structures).

FIG. 20 shows the device from the mother patent Ser. No. 17/501,291, with the first supporting structure relabeled as Ex (for extractor, which is the application of this continuation-in-part patent application). It depicts two examples of second supporting structures, labeled as PA. On both the first and second supporting structures there are electrodes of the first and second types (140_t1 and 140_t2). This patent application is a variation of the mother application Ser. No. 17/501,291, where the first supporting structures are extractors Ex, instead of simple electrode supporting structures.

FIG. 16 shows a shirt supporting structure that is of the type here called second supporting structure, with several electrodes on it. Such a second supporting structure could be used both for the case of a breast biopsy, which is the particular implementation we are using as examples here, or for other types of biopsies elsewhere in the abdomen or in the chest of the unfortunate patient.

Many variations are possible, all of which are intended to be covered by this patent application.

Figure 12:
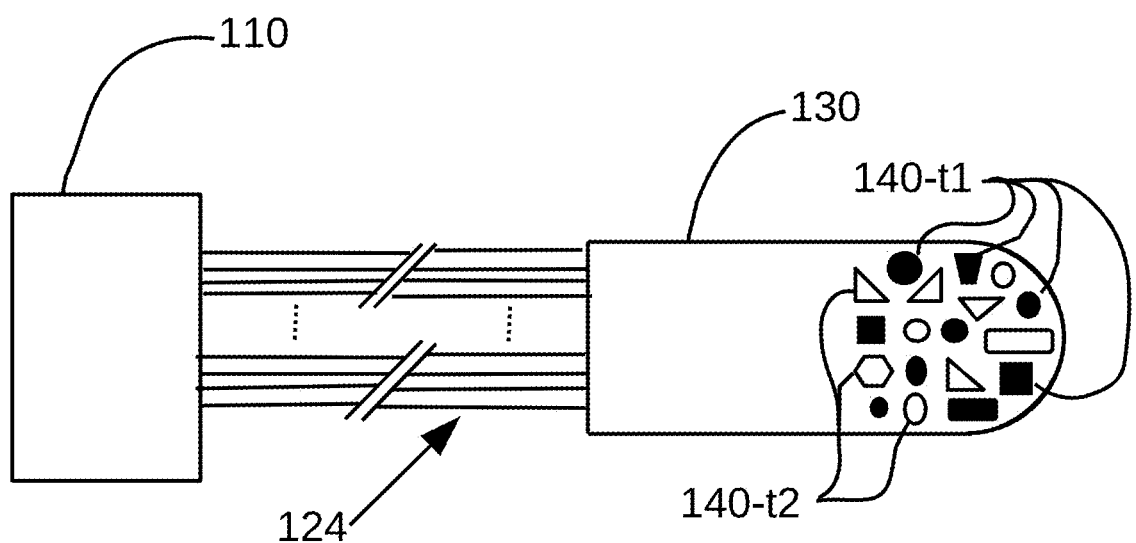
FIG. 12 shows a stimulator of our invention for the brain (DBS).

Another embodiment of our invention is application to DBS (Deep Brain Stimulation). In this application the objective is to disrupt the anomalous neurons firings that cause the tremor characteristic of Parkinson's disease, or of what is known as essential tremor. One of the possible solutions is to place an electrode on a chosen target area in the brain then superimpose a current of frequency around 200 Hz on it. FIG. 12 shows a brain-type stimulator we call picafina, similar in structure to prior art stimulators with 4 rings at their distal extremity (Butson and McIntyre (2006)) but with the equivalent electrode described for the heart cordum: active and passive (field-shaping) electrodes. The objective for the Deep Brain Stimulator (DBS) is to adjust the electric field in the vicinity of the brain electric stimulator, which we call picafina or picafina-style stimulator, to the shape of the particular target volume, which could be the sub-thalamic nucleus (STN), the globus pallidus internus (GPi) or any other. Much effort has been put on the solution of this problem, the solution of which has evaded the practitioners of the art for decades—see, for example, Butson and McIntyre (2006). It can be seen at Butson and McIntyre (2006) that the best solution proposed is still a symmetric field. Such a symmetric field fail to offer a maximum electrical stimulation in any case, particularly when the electric stimulator happens to have been implanted off-center. As discussed by Butson and McIntyre (2006), this is, in fact, a most common occurrence, due to the small size of the target volumes and their location deep in the base of the brain (for DBS), which is also not directly observed by the surgeon, which inserts the electric stimulator through a one-cm diameter hole drilled at the top of the skull, from where she tries to guide the stimulator tip to the desired target volume (but they call it target area or simply area for some obscure reason). Our invention allows for more control of the electric field around the stimulator, which in turn, allows for better clinical results. More modern stimulators, e.g. the ones introduced by *Sapiens* Neuro (www.Sapiens-Neuro.com) as for example H. C. F. Martens U.S. Pat. No. 9,095,698 of 2015 Aug. 4 are capable of creating an asymmetric electric charge distribution in the target area, but fail to decouple the control of the electric field from the injection of the electric charges, therefore failing to maximize the results.

Figure 13:
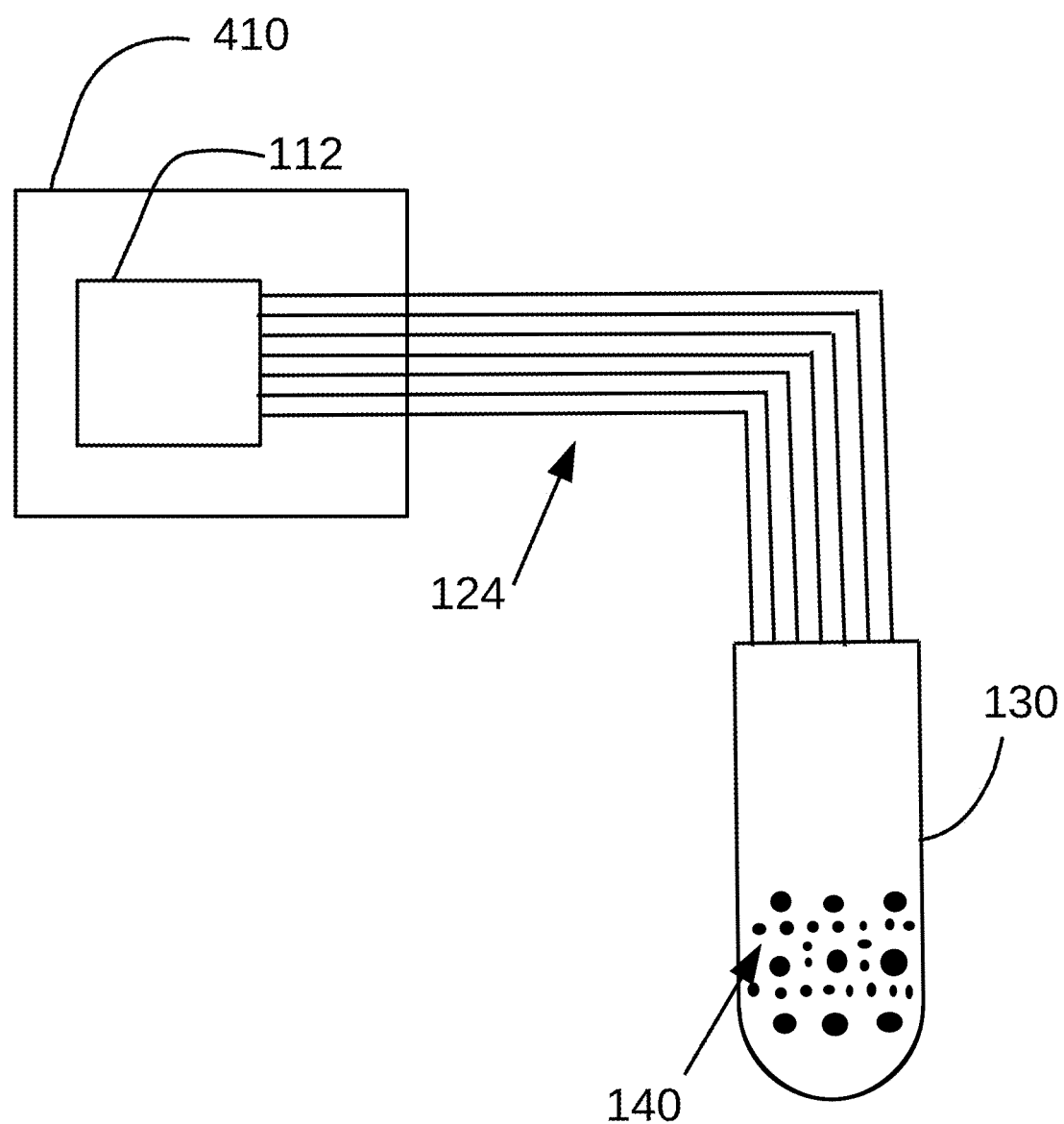
FIG. 13 shows another view of a brain version of our stimulator.

FIG. 13 shows another schematic view of the picafina brain-style stimulator, though other than the stimulator contour, which reminds the DBS stimulating support picafina, the schematic representation could transfer to the heart-type cordum, to the planar type, which in turn may be flexible as a plane bed sheet, and any other. In it, 110 is a hermetically sealed box, which in prior art is normally made of titanium or any other bio-compatible material, the energy storage unit BAT1 (battery) and the microprocessor MP1 are omitted for simplicity, 124 is the power (voltage or current) wires, one for each electrode, potentially at different voltage/current levels, 130 the picafina stimulator-type, and 140 the plurality of electrodes, some of which are active, others are of the field-shaping type, potentially of the sub-surface type, which in this figure are not differentiated between active and field-shaping, for simplicity.

Figure 14:
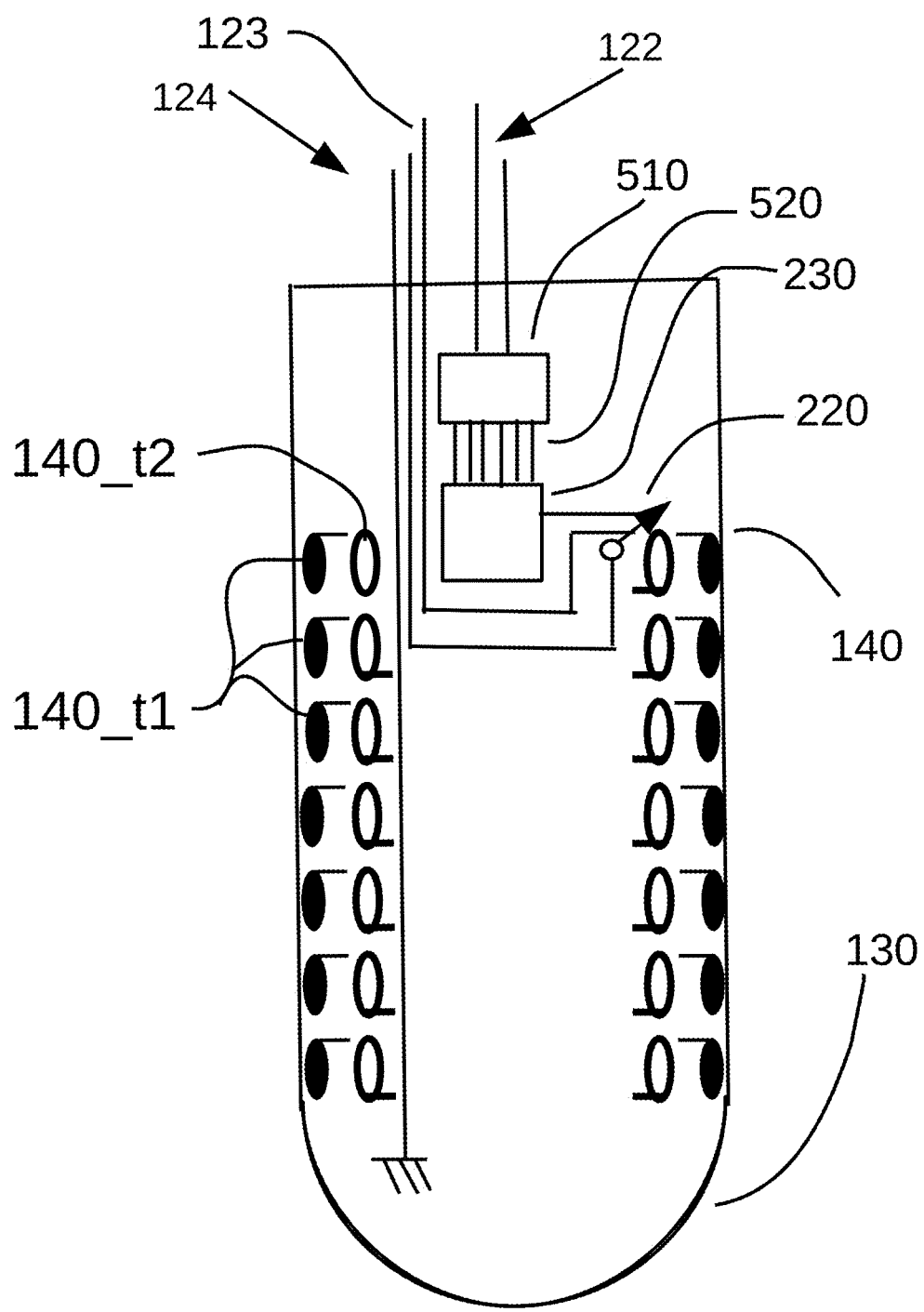
FIG. 14 shows another view of a brain version of our stimulator with some sub-surface field-shaping electrodes of our invention.

FIG. 14 shows another schematic diagram of a picafina brain-style stimulator of our invention with the active electrodes 140_t1 at the surface of the supporting structure and the sub-surface field-shaping electrodes 140_t2, underneath the active electrodes 140_t1. FIG. 14 displays a cut-away view of a picafina with electrodes inside the body of the supporting structure. Note also that FIG. 14 omits displaying electrodes on the side of the viewer, for difficulty of making such a drawing, and on the back side, for a similar reason and also for being invisible on the back side. FIG. 14 is a schematic representation, not a real rendition with all details, showing a cut-away view, the cut made by a plane containing the axis along the long dimension of the picafina and parallel to the viewer. The same principles are applied to the cordum heart-type stimulator and to other variations of it.

FIG. 20 displays the innovative protruding arms PA or second supporting structures, of a variation of our invention. FIG. 20 is a schematic representation of either a device for extracting tissues for biopsies, or a picafina, known by Medtronic as lead, a non-specific name we avoid in favor of picafina, including the multiple electrodes introduced by our earlier patents (e.g., "Method and means for connecting a large number of electrodes to a measuring device" U.S. Pat. No. 8,335,551, issued on 18 Dec. 2012 and also later by H. C. F. Martens U.S. Pat. No. 9,095,698 of 2015 Aug. 4), but with the modification of the protruding arms PA, or second supporting structures, which may be permanently protruding out or may be retractable to the inside of the extractor Ex or the main support picafina. The advantages of the protruding arms PA, or second supporting structures, are multiple, in particular (1) the possibility of injecting stimulating electric charges from another location outside the main body of the picafina supporting structure, and (2) the possibility of utilizing type-2 electrodes located outside the picafina main supporting structure, which allows for a better control of the electric field shapes and therefore a better control of the motion, direction and speed of the injected electric charges, and therefore a better control of the stimulated volume. This control of the stimulated volume is crucial for the extractor Ex, because of the possibility of pain felt by the patient during the procedure. This pain may require an additional second injection of anesthetics (4), which creates problems for the surgeon, due to the increased time for the procedure, and problems for the patient, because nobody likes to experience pain. A device that is capable of injecting soothing electric currents, TENS-type, would be perfectly capable of taking care of this extra smaller pain during the procedure. The reader should be warned that we are not proposing electrical currents (TENS) as a substitute for the chemical anesthetics, but only the use of the electric charge to add a second level of pain depressor to the larger pain depressor caused by the anesthetics. This control of the stimulated volume is crucial for DBS and for tissue extractor, as acknowledged by so many researchers in the field, e.g., M. Kloc et al. "Prevalent placement error of deep brain stimulation electrode in movement disorders" *Bratisl Med J.* v. 118, page 647 (2017). In this article M. Kloc analyses the consequences of either misplacement of the stimulating electrode (picafina) or its later displacement due to accelerations of the head during the life of the patient, both of which occur in clinical devices implanted in people. Our protruding arms PA, offer the options of other positions for the electrodes used for stimulation, from any of the existing electrodes at the surface of the picafina ("lead" using the bad name used by Medtronic). This is true for both inaccurate initial positioning at the implanting time, which is very common, or due to later movement of the picafina supporting structure due to accelerations of the brain. So, our protruding arms PA offer two separate and important advantages over the existing devices: (1) options for more locations from which to inject the electrical stimulation to "make up" for the common inaccurate initial implant location, and also (2) for readjustment of stimulation locus later, due to expectable motions of the picafina supporting structure due to head accelerations. The reader is here reminded that all acceleration is associated with an external force (Newtons's $2^{nd}$ law), which is the cause of the displacement of the picafina, and that the acceleration can be a small one, like just turning the head, which is too small an acceleration to cause a motion of the picafina, or larger accelerations, as due to a fall—and the reader will appreciate that the wearers of DBS are generally old, and more prone to falls than a younger person, also less capable of bracing themselves, as compared to a younger person, therefore suffering a larger impact than a younger person would when she/he latter braces her/himself to decrease the impact of the fall.

For the case of retractable protruding arms PA, the protruding arm PA may retract backward along its own axis and into the picafina supporting structure, or the protruding arms PA may be bent back to a position along the main supporting structure picafina. This could be achieved, for example by a spring that apply an outward force on the protruding arms PA and a small cable that runs along the length of the picafina to its anchoring place at the top of the head. When the surgeon implants the picafina the cable may be pulled tight, keeping the protruding arms PA inside the picafina, then, when the surgery is completed the neurosurgeon releases the tension on the cable, with which action the spring forces the protruding arm out from the picafina body 132. Or a spring could be positioned to rotate the protruding arms PA around their base to a final position as shown in FIG. 20, while a cable would keep such a spring tight back, keeping the protruding arms PA tight against and parallel to the picafina supporting structure 132. Or, instead of a cable controlled by the neurosurgeon, the motion could be controlled by a small electric motor, or many equivalent methods. This variation could be adjusted to keep the protruding arm PA closer to or further away from the picafina supporting structure 132, which, in turn, would vary the position of the electrodes located at the protruding arms PA. Similar controls can exist and be available for a surgeon performing breast biopsies, or other types of biopsies as well.

Another variation for the protruding arms PA is to use nanowires protruding out from the main supporting picafina body. These nanowires may be permanently extending out, as hairs follicles protruding out of the skin of animals, or they may be retractable.

The reader should pay attention that the protruding arms PA of our invention point forward. This is an important difference of my invention from the so-called tines that are part of many heart pacemakers, which point backward, not forward. The tines used in the heart pacemakers have no electrical function, as our protruding arms PA have; the tines have a purely mechanical function, which is to anchor the electrodes at the end of the wire in a fixed place in the heart. The tines of the heart pacemakers have a similar function as the barbs on arrows of the past, before the western men adapted to the new use of killing, the powder used by the Chinese of the past to make beautiful displays for the lunar new year and other celebrations. Some of the arrows had barbs on them to keep the arrow in place inside the unfortunate animal, once the arrow penetrated, which is the same function of the tines on the electrodes of the heart pacemakers: to keep the heart pacemaker in place once it is placed inside the heart. The hooks used to fish usually have the same, with variations, and so does the ship anchor, to keep them in place as well, in the mouth of the poor fish and in the sand below the ship to keep this latter from moving away. Our invention has a protruding arm PA that points not backward but forward—which is a fundamental difference from the heart pacemakers' tines. The protruding arms PA are not used to keep the electrodes in place, but rather to encircle the electrode head, from which position they are perfectly suited to apply an electric field on the electric charges used for electrical stimulation—so different than the tines used by the heart pacemakers. Moreover, because the electrical stimulation used for brain, as in DBS (Deep Brain Stimulation) is required to be limited to such a small volume (the neuro guys say small area . . . ), it follows that the protruding arms PA are ideally suited for this purpose of keeping the electrical stimulation confined to a small desirable target volume, which could be, for example, the Globus Pallidus Internus, or the subthalamic nucleus, which are a few mm in size only. The same arguments and statements apply for the extractor Ex, used to extract samples from a breast or other organs for later biopsies to determine malignancy.

The protruding arms PA may be all at the same distance from the tip of the DBS stimulator, as shown in FIG. 20, or there may exist a second group of protruding electrodes more away from the tip (below the protruding electrodes shown at FIG. 20). Our invention is not limited to one group of protruding arms PA, but there may have more then one group. These observations apply equally well for the extractor Ex, which is the object of the current invention. remove underline.

Also, FIG. 20 shows protruding arms PA only to the right and to the left, which is solely for simplification of the figure. Protruding arms PA exists all around the picafina supporting structure, perhaps 4 protruding arms PA, 90 degrees spaced around, or 6 protruding arms PA, 60 degrees spaced around, etc. These observations apply equally well for the extractor Ex, which is the object of the current invention.

It is understood that the electrodes located at the protruding arms PA may be type-1 or type-2, or type-3, and that the type-2 electrodes may be located at the surface of the supporting structure or under the surface of the supporting structure. These observations apply equally well for the extractor Ex, which is the object of the current invention.

The electrodes for DBS can be of different size, of different shapes and also randomly distributed on the surface of the supporting structure or picafina, or they can be of uniform size and shape, perhaps to decrease manufacturing cost, for example, or to simplify the internal wiring, or any other reason. Given the small size of the electrodes, random shape of them is of smaller effect than their numbers, while the use of the two types of electrodes, active or type-1 electrodes and passive or type-2 electrodes are of major importance, given that the latter only change the electric field shape around the stimulator device. These observations apply equally well for the extractor Ex, which is the object of the current invention.

The reader will notice that the DBS application is a natural adaptation of all that is described for the cordum heart pacemaker, yet the DBS needs no time control of a sequential muscular contraction, so it is simpler to program and to use than the heart cordum. A multiplicity of electrodes, of variable shapes and sizes, each associated with a unique wire, which is used to select which electrode is turned on, which electrode is turned off, both for type-1 (active) and type-2 (field-shaping). Likewise for the cordum heart pacemaker, the DBS incarnation uses two types of electrodes: a first type, 140_t1 or active type, capable of injecting a current, and a second type, 140_t2 or field-shaping type, which is insulated, not capable of injecting any current (though always there is a small leak current due to insulator imperfections), but which is much useful for creating the vector field around the electrode, which, in turn, determine the 3-dimensional path for the injected current. These observations apply equally well for the extractor Ex, which is the object of the current invention.

Another possible application for the invention is for appetite control. In this application there are two possibilities: electrical stimulation on the stomach, and brain stimulation at the locations which are known to control the appetite. In the former case the added electrical stimulation may be turned on before a meal, and the electrodes are selected to affect the neurons that send information to the brain regarding the current amount of food in the stomach, which in turn modulate the appetite. If the stimulation is capable to fool the brain, the individual will feel a decreased urge for food, eat less, and lose weight on the long run. This has been used in humans already. The second case, brain stimulation to control the appetite has been only used in animals so far, and with success. For stomach stimulation the shape of the stimulator should be a flat deformable shape (as in a bed sheet) to conform to the curvature of the stomach and its enervations. For direct brain control it may be similar to the DBS.

Another possible application is for cortical brain stimulation, in which case the stimulator has a flat shape to adjust to the cortical application.

Another possible application is for pain control, an improvement of a known device known as TENS (Transcutaneous Electrical Neural Stimulation). In this application the objective is to control superficial pain, as skin pain, and it has used for deeper pain too, as muscle pain. The area (here it is really an area, the surface area of the skin in question, not what the neurologists call area, which is a volume) in question is in this case surrounded by electrodes attached to the skin, from which there is a current flow. Old art used large electrodes, which did not allow for a control of the current path. In this case our invention discloses a large number of small electrodes which are on the surface of the applied patch. Likewise the cordum heart pacemaker, these small electrodes are numbered and individually activated by their dedicated wires which is under control of the controlling electronics, are of three types (type-1, or active, and type-2 and type-3, or field-shaping), and can likewise be turned on or off at any of a plurality of voltages/currents or off (zero voltage/current). With a wise selection of the active electrodes, it is possible for the medical practitioner to ameliorate the pain felt by the patient in a more effective way than currently used TENS devices.

Another possible application is for cochlear implants. The problem of cochlear implants is that the electric charges (the electrical stimulation) originating from a particular electrode spreads out as it propagates to the neurons in front of it, with the consequence that the electric charge stimulates the intended neuron and also nearby neurons. For this application what is need is an electric field that forces the artificial electrical stimulation to propagate inside a well-confined line (in reality a small cylinder) from the electrode to the intended neuron in front of it. In such a case a set of electrodes behind the active electrode could cause a force field that cajoles the ions to propagate forward toward the intended neuron. For example, a circular passive electrode 140_t2 with center behind the active electrode would create such a desirable electric field that keeps the ions propagating forward.

The individual electrodes, which in the main embodiment are randomly spread on the supporting structure (picafina), and are of various shapes and sizes, can be all of the same shape and/or same size, and/or can be arranged on an orderly arrangement too. In such a case the advantage of maximal symmetry breaking is not achieved, but some partial symmetry breaking is still obtained with the selection of particular electrodes as the points from which to initiate the stimulation, and the selection of other particular (insulated) electrodes from which to originate the field shaping lines. Cost and other factors could determine a simpler regular electrode arrangement. More orderly arrangements of the electrodes than the arrangement disclosed in the main embodiment, which provides maximal advantage, are still in the scope of the invention.

Persons acquainted with the art of symmetry will recognize that for very small electrodes with small spacing between each, there is little gain if compared with larger electrodes of variable shape and sizes, as particular sets of smaller electrodes can approximately create the shape of a larger electrode of any arbitrary shape. Cost and programming time may dictate one type of another of electrode, and their size and placement, while these variations are still covered in the scope of the invention.

The relative distribution of the electrodes of type-1 and type-2 and type-3 (current injecting electrodes and electric field shaping electrodes, or magnitude and direction determining electrodes) is random in the main embodiment of this invention, with the active 140_t1 electrodes at the surface and the field-shaping 140_t2 and 140_t3 electrodes underneath the active electrodes, but it is possible to have field-shaping electrodes at the surface too.

Figure 15B:
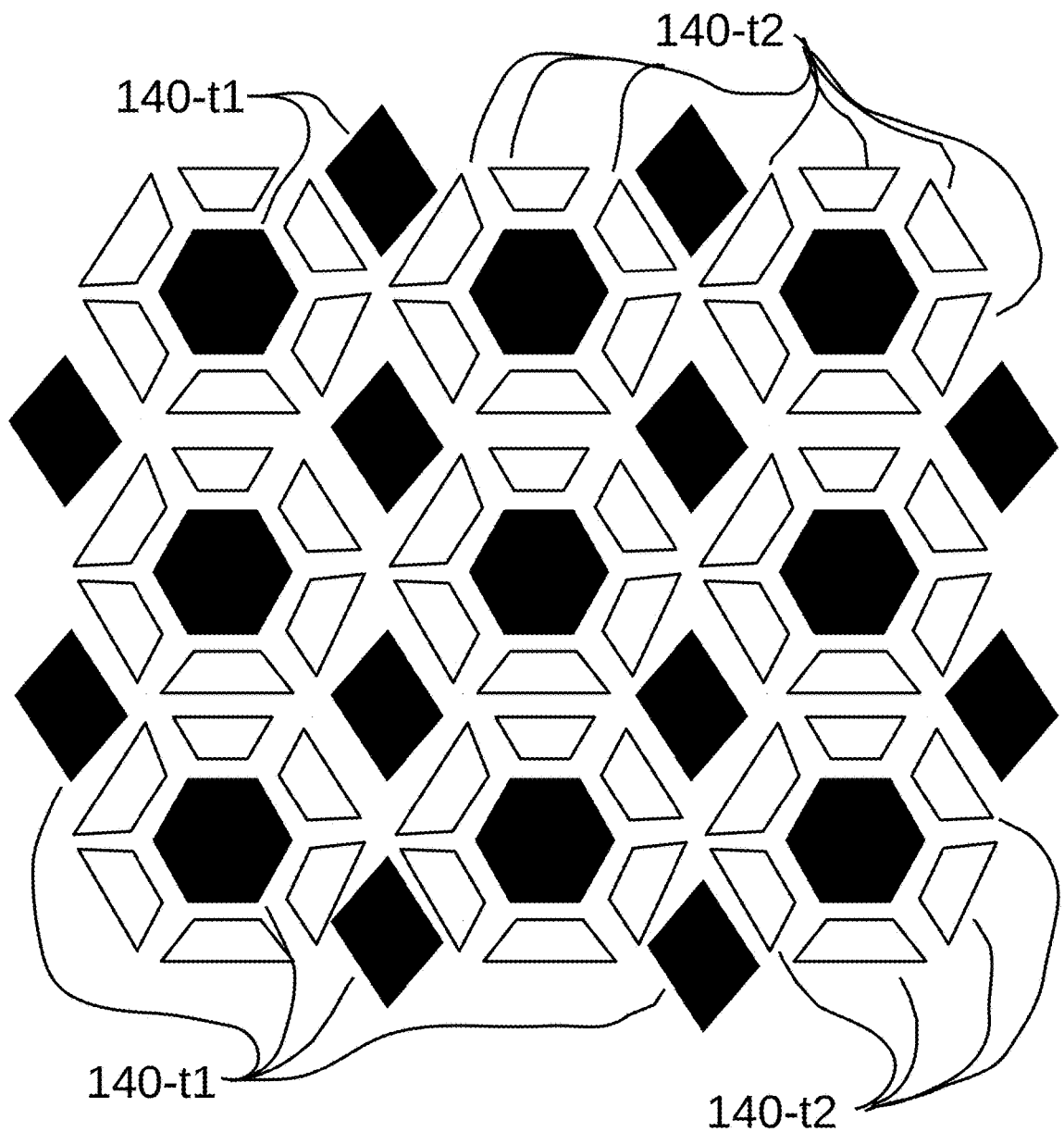
FIG. 15B shows a few possible electrode configuration for electrical stimulation.

One interesting regular pattern for the electrodes is the hexagonal pattern, which is shown in figure FIG. 15B, and other variations of it, as the octagonal pattern, shown in figure FIG. 15A.

Persons familiar with the art understand that the hexagonal pattern displayed at figure FIG. 15B is just one of the many possibilities. Triangular arrays square arrays, rectangular arrays, and others are possible, these being examples of arrays that completely fill the space. But the individual units do not have to even completely fill the available space, because maximal asymmetry (maximal lack of symmetry, or maximal symmetry breaking) is achieved with random distribution of electrodes.

CONCLUSION, RAMIFICATIONS, AND SCOPE OF INVENTION

Another way to see the control of the paths of the current in the heart, or the extent of electrical stimulation in brain DBS, etc., is to look at the active electrodes determining the magnitude (and also the direction in a limited way too, because the active electrodes also contribute to the electric field vector) and the field-shaping electrodes determining the direction and speed only of the current injected by the former, active electrodes. In this view one considers the stimulating current as a vector which follows the electric field lines.

Other options are possible for the marker 140-*tm* that indicates the angular position of the cordum as implanted. For example, all the electrodes may have enough X-ray opacity to show in the fluoroscopic images taken during the heart pacemaker implantation. Or one or more or the anchoring arms 131 may be smaller (or larger), or each anchoring arm may be of a different length and/or diameter, to allow their identification.

The main embodiment for heart stimulation uses a simple version of stimulation, which is fixed and continuous, of the type of the old heart pacemakers. It is possible to have stimulation on demand too, as many current pacemakers have, which is based, for example, on activating the stimulation only when the natural pacemaker becomes insufficient, or stops, or becomes erratic. This is called stimulation on demand, easily incorporated in our invention that already contains a microprocessor capable of implementing such decisions. Such extensions are part of the current art of heart pacemakers and may or may not be incorporated in our invention. Our invention is independent of stimulation on demand.

One skilled in the relevant art, however, will readily recognize that the invention can be practiced without one or more of the specific details, or with other methods, etc. In other instances, well known structures or operations are not shown in detail to avoid obscuring the features of the invention. For example, the details of the wiring can be realized in several different ways, as coiled wires, as printed circuit wires, etc., many or most of which are compatible with the invention, and therefore the details of these, and other details are not included in this patent disclosure.

REFERENCES (1) LizhiXu, . . . Igor R. Efimov et al. "3D multifunctional integumentary membranes for spatiotemporal cardiac measurements and stimulation across the entire epicardium" Nature Comm Vol 5 Pg 3329 (March 2014).
(2) Colleen Clancy and Yang Xiang "Wrapped around the heart" Nature Vol 507 pg 43 (6 Mar. 2014).
(3) Pierre Martin "Une membrane artificielle pour surveiller le coeur" La Recherche (1 Mai 2014).
(4) "Pain in different methods of breast biopsy: Emphasis on vacuum-assisted breast biopsy" The Breast, Volume 17, Issue 1, February 2008, Pages 71-75

The invention claimed is:

1. A device for an electrical stimulation of a target area or a target volume of an animal, comprising:
   a. an electric stimulating assist system comprising: a body with at least one first supporting structure and at least one second supporting structure, an electric energy storage unit, a control unit,
   b. the at least one first supporting structure with a proximal extremity and a distal extremity, configured to be anchored in the vicinity of the target area or the target volume, wherein,
   c. the at least one first supporting structure is configured to keep in fixed position a minimum of one electrode belonging to any of type-1 and/or type-2 and/or type-3 electrodes, electrically coupled to the energy storage unit and to the control unit,
   d. the type-1 electrodes are capable of injecting electric charges capable of propagating on its surroundings, while the type-2 electrodes and type-3 electrodes are incapable of injecting electric charges on their surroundings,
   e. the at least one second supporting structure that either projects out from the first supporting structure and points forward from the distal extremity of the first supporting structure, or points to the side from the first supporting structure, or envelops part of or totally the first supporting structure,
   f. the at least one second supporting structure is configured to support the at least one electrode of type-1 and/or type-2 and/or type-3,
   wherein each of the minimum of one type-1 and/or type-2 and/or type-3 electrodes with a volume and a surface, below the surface or at the surface of the first supporting structure and/or the second supporting structure, are connected electrically with wires to the electric energy storage unit, and configured to produce to produce an electric potential at the minimum of one type-1 and/or type-2 and/or type-3 electrodes located at the first supporting structure or at the second supporting structure,
   wherein the surfaces of the minimum of one type-2 and/or type-3 field-shaping electrodes are covered by an electrically insulating layer configured to prevent electric charges from moving out of any of the minimum of one type-2 and/or type-3 field-shaping electrodes,
   wherein the minimum of one type-2 and/or type-3 field-shaping electrodes are adapted to project an electric field in a space surrounding the electric stimulating assist system,
   wherein the electric field projected by the minimum of one type-2 and/or type-3 field-shaping electrodes is configured to apply a force on the propagating electric charges injected by the type-1 electrodes or naturally occurring electric charges in the space surrounding the body of the electric stimulating assist system, guiding the propagating electric charges on a target path and/or to keep the propagating electric charges inside a target volume.

2. The device of claim 1 further comprising one or more additional type-2 field shaping electrode located at the surface of the wires that connect the electric energy storage unit to the supporting structure and/or one or more additional type-3 field shaping electrode located under the surface of the wires that connect the electric energy storage unit to the supporting structure.

3. The device of claim 1 further comprising an additional type-2 and/or type-3 field-shaping electrode coupled to a skin of an animal in which the electric stimulating assist system is implanted.

4. The device of claim 1 wherein the second supporting structure partly or totally surrounds the distal extremity of the first supporting structure, the first supporting structure having a tip at its distal extremity.

5. The device of claim 4 wherein the second supporting structure partly or totally surrounds the target area or the target volume of the animal and is configured to cover more than 50% of the surface of the target area or the target volume of the animal.

6. The device of claim 4 wherein the second supporting structure is in the shape of a truncated cone opening towards the distal extremity of the first supporting structure.

7. The device of claim 4 wherein the second supporting structure conforms to the shape of a female breast.

8. The device of claim 4 wherein the second supporting structure configured to be attached to the first supporting structure that is configured to be anchored in the vicinity of the target area or the target volume of the animal partly or totally surrounds a target area or target volume at the thorax or at the abdomen of the animal.

9. The device of claim 4 wherein the second supporting structure configured to be attached to the first supporting structure that is configured to be anchored in the vicinity of the target area or the target volume of the animal partly or totally surrounds a target area or target volume at the spinal cord of the animal.

10. The method of claim 9 further comprising one or more additional type-2 field shaping electrode located at the surface of the wires that connect the electric energy storage unit to the electric stimulating assist system and/or one or more additional type-3 field shaping electrode located under the surface of the wires that connect the electric energy storage unit to the electric stimulating assist system.

11. The method of claim 10 wherein the second supporting structure is attached to the first supporting structure configured to be anchored in the vicinity of the target area or the target volume and wraps around a neck of the animal.

12. The method of claim 10 wherein the second supporting structure is attached to the first supporting structure configured to be anchored in the vicinity of the target area or the target volume and wraps around a thorax or an abdomen of the animal.

13. The method of claim 10 wherein the second supporting structure is attached to the first supporting structure configured to be anchored in the vicinity of the target area or the target volume and wraps around a breast of the animal.

14. The method of claim 10 wherein the second supporting structure is attached to the first supporting structure and is configured to be anchored in the vicinity of the target area or the target volume and wraps around the target area or the target volume of the animal covering more than 10% of the surface of the target area or the target volume of the animal.

15. The method of claim 10 wherein the second supporting structure is attached to the first supporting structure and is configured to be anchored in the vicinity of the target area or the target volume and wraps around the target area or the target volume of the animal covering more than 1% of the surface of the target area or the target volume of the animal.

16. The method of claim 9 further comprising an additional type-2 and/or type-3 field-shaping electrode coupled to a skin of the animal in which the electric stimulating assist system is implanted.

17. The method of claim 9 wherein the second supporting structure is attached to the first supporting structure configured to be anchored in the vicinity of the target area or the target volume and partly or totally wraps around the target area or the target volume of the animal.

18. The device of claim 4 wherein the second supporting structure configured to be attached to the first supporting structure that is configured to be anchored in the vicinity of the target area or the target volume of the animal partly or totally surrounds a target area or target volume at the neck of the animal.

19. A method of an electrical device of claim 1, the method comprising:
   providing the electrical device of claim 1,
   wherein field shaping electrodes of the electric stimulating system are located at the first supporting structure or at the second supporting structure, are configured to apply a force on either the propagating electric charges injected in an animal by the electric stimulation system, or electric charges naturally produced by the animal.

* * * * *